(12) United States Patent
Myeong et al.

(10) Patent No.: US 9,725,739 B2
(45) Date of Patent: Aug. 8, 2017

(54) METHOD FOR PREPARING D-CHIRO-INOSITOL USING MICROBES

(71) Applicant: DY NATURAL CO., LTD., Daejeon (KR)

(72) Inventors: Hyun Koon Myeong, Daejeon (KR); Sang-Hwal Yoon, Chungcheongnam-do (KR); Hyeon-Seo Lee, Gyeongsangnam-do (KR)

(73) Assignee: DY NATURAL CO., LTD., Daejeon (KR)

( * ) Notice: Subject to any disclaimer, the term of this patent is extended or adjusted under 35 U.S.C. 154(b) by 0 days.

(21) Appl. No.: 14/431,396

(22) PCT Filed: Sep. 26, 2013

(86) PCT No.: PCT/KR2013/008637
§ 371 (c)(1),
(2) Date: Mar. 26, 2015

(87) PCT Pub. No.: WO2014/051358
PCT Pub. Date: Apr. 3, 2014

(65) Prior Publication Data
US 2016/0017376 A1    Jan. 21, 2016

(30) Foreign Application Priority Data
Sep. 26, 2012 (KR) .................. 10-2012-0107278

(51) Int. Cl.
| | | |
|---|---|---|
| *C12P 7/04* | (2006.01) | |
| *C12P 7/02* | (2006.01) | |
| *C12P 7/18* | (2006.01) | |
| *C12N 9/04* | (2006.01) | |
| *C12N 9/90* | (2006.01) | |
| *C07K 14/195* | (2006.01) | |
| *C07K 14/255* | (2006.01) | |
| *C07K 14/32* | (2006.01) | |

(52) U.S. Cl.
CPC .............. *C12P 7/02* (2013.01); *C07K 14/195* (2013.01); *C07K 14/255* (2013.01); *C07K 14/32* (2013.01); *C12N 9/0006* (2013.01); *C12N 9/90* (2013.01); *C12P 7/18* (2013.01); *C12Y 101/01018* (2013.01)

(58) Field of Classification Search
None
See application file for complete search history.

(56) References Cited

FOREIGN PATENT DOCUMENTS

| JP | 2006-141216 | 6/2006 | ................ C12P 7/18 |
| WO | WO 02-055715 | 7/2002 | ............. C12N 15/61 |

OTHER PUBLICATIONS

Lin et al. (Br. J. Nutr., 2009, 102(10), 1426-1434).*
Baillargeion et al. (Diabetes Care, 2006, 29(2), 300-305).*
"Myo-inositol 2-dehydrogenase [*Agrobacterium* sp. ATCC 31749]", GenBank Accession No. EGL61813 (May 23, 2011).
"Major myo-inositol transporter IolT [*Bacillus subtilis* subsp. *subtilis* str. 168]", GenBank Accession No. NP_388504 (Dec. 22, 2014).
Yoshida, et al. (2006) "Genetic modification of *Bacillus subtilis* for production of D-*chiro*-Inositol, an investigational drug candidate for treatment of type 2 diabetes and polycystic ovary syndrome." *Applied and Environmental Microbiology*, 72(2):1310-1315.
International Search Report (ISR) dated Feb. 5, 2014 in PCT/KR2013/008637 with English translation.

* cited by examiner

*Primary Examiner* — Hope Robinson
(74) *Attorney, Agent, or Firm* — Harness, Dickey & Pierce, P.L.C.

(57) ABSTRACT

The present invention relates to a method for preparing D-chiro-inositol from myo-inositol by using a transformed host cell which expresses enzymes such as a myo-inositol transporter, inositol dehydrogenase, and inosose isomerase. According to the method of the present invention, myo-inositol can be converted into D-chiro-inositol at a high yield.

6 Claims, 13 Drawing Sheets

0.1% D-chiro-inositol of Standard sample 0.1% D-chiro-inositol prepared

METHOD FOR PREPARING D-CHIRO-INOSITOL USING MICROBES

CROSS-REFERENCE TO RELATED APPLICATIONS

This application is a national phase application of PCT Application No. PCT/KR2013/008637, filed on Sep. 26, 2013, which claims the benefit and priority to Korean Patent Application No. 10-2012-0107278, filed Sep. 26, 2012. The entire disclosures of the applications identified in this paragraph are incorporated herein by references.

REFERENCE TO A SEQUENCE LISTING

Applicant hereby submits, in compliance with sequence rules 37 C.F.R. §§1.821-1.825, the required Sequence Listing. A copy of the Sequence Listing is being submitted in computer readable format as required by 37 C.F.R. §1.182 (e).

This application contains references to amino acid sequences and/or nucleic acid sequences which are being submitted concurrently herewith as the sequence listing text file 61585544_1.TXT file size 62 KiloBytes (KB), created on 22 Sep. 2015. The aforementioned sequence listing is hereby incorporated by reference in its entirety.

FIELD

The present invention relates to a method for preparing D-chiro-inositol using microbes, and more particularly, to a method for preparing D-chiro-inositol from myo-inositol by means of a transformed microbe host cell.

BACKGROUND

D-chiro-inositol (cis-1,2,4-trans-3,5,6-cyclohexol) is a stereoisomer of myo-inositol (cis-1,2,3,5-trans-4,6-cyclohexanehexol) in a form that 3-hydroxyl group is epimerized (FIG. 1). D-chiro-inositol, which is a main component of inositol-phosphoglycan (IPG), has been reported as an important medium of insulin signal transduction and also known as being effective in the treatment of type II diabetes. D-chiro-inositol is mainly found in eucaryota and biosynthesized by means of the epimerization of myo-inositol.

D-chiro-inositol is mainly prepared by means of the hydrochloric acid hydrolysis of D-pinitol or kasugamycin (U.S. Pat. No. 5,827,896, U.S. Pat. No. 5,091,596, U.S. Pat. No. 5,463,142 and U.S. Pat. No. 5,714,643). However, as raw materials, D-pinitol or kasugamycin is expensive and organic synthesis (U.S. Pat. No. 5,406,005, WO 96/25381) is also known, but not economically feasible due to difficult separation of by-products.

Yamamoto et al presented a method for converting myo-inositol into chiro-inositol by using germs which express MI epimerase of *Agrobacterium* sp. AB10121 (JP2001-006878, WO2002/055715). The method of Yamamoto et al is capable of preparing D-chiro-inositol from myo-inositol at an approximately 15% yield.

Throughout the present specification, a number of papers and patent documents are referred to and their citations are indicated. The disclosed contents of cited papers and patent documents are included herein by reference in this entirety, so that the related art and the contents of the present invention could be more clearly described.

SUMMARY

The inventors have concentrated research and development efforts on preparing chiro-inositol from myo-inositol by using microbes. As a result, the inventors have come to complete the present invention by confirming that it is possible to prepare D-chiro-inositol from myo-inositol at a high yield by using a transformed host cell with a recombinant expression vector including a myo-inositol transporter, inositol dehydrogenase and inositol coding gene.

Therefore, the object of the present invention is to provide a method for preparing D-chiro-inositol from myo-inositol by using a transformed host cell.

Another object of the present invention is to provide a transformed host cell which expresses a myo-inositol transporter, inositol dehydrogenase and inosose isomerase.

Yet another object of the present invention is to provide a composition for preparing D-chiro-inositol including the transformed host cell.

And, still yet another object of the present invention is to provide a kit for preparing D-chiro-inositol including a recombinant vector with a DNA sequence, which codes a myo-inositol transporter, inositol dehydrogenase and inosose isomerase.

The objects and advantages of the present invention will be more clearly described in the Summary of the Invention, Claims and Drawings as shown below.

TECHNICAL SOLUTION

According to one aspect of the present invention, there is provided a method for preparing D-chiro-inositol from myo-inositol, the method including: (a) obtaining a transformed host cell by transforming a host cell with (i) a recombinant vector including a myo-inositol transporter coding DNA sequence operatively linked to a promoter; (ii) a recombinant vector including an inositol dehydrogenase coding DNA sequence and an inosose isomerase coding DNA sequence operatively linked to a promoter; and (b) culturing the transformed host cell in a medium including myo-inositol.

Hereinafter, the present invention will be described in more detail according each of steps.

(a): obtaining a transformed host cell by transforming a host cell with a recombinant vector including a myo-inositol transporter, inositol dehydrogenase and inosose isomerase coding DNA sequence.

The term "myo-inositol transporter" used in the present specification means a transport enzyme which transports myo-inositol into a cell. Most cells have an inositol-transporting system, which allows inositol in a medium to be absorbed into a cell. The myo-inositol transporter has been found in various cells ranging from mammalian cells to bacteria. It is reported that a myo-inositol transporter gene has been separated from bacteria such as *Aerobacter aerogenes* (Deshusses, J., and Reber, G., 1972, Biochim. Biophys. Acta 274, Bacteriol. 126, 243-250), *Pseudomonas putida* (Reber, G., Belet, M., and Deshusses, J., 1977, J. Bacteriol. 131, 872-875), *Pseudomonas* species (Gauchat-Feiss, D., Frey, J., Belet, M., and Deshusses, J., 1985, J. Bacteriol. 162, 324-327). And it is reported that a myo-inositol transporter gene has been separated from even yeasts such as *Saccharomyces cerevisiae* (Nikawa, J., Nagumo, T., and Yamashita, S. (1982) J. Bacteriol. 150, 441-446). It is also known that a myo-inositol transporter exists in a major type and a minor type.

The myo-inositol transporter used in the present invention may be the one derived from a mammalian cell, a yeast cell or bacteria, and preferably a transporter derived from bacteria. More preferably, it can be the myo-inositol transporter separated from *Bacillus subtilis, Salmonella typhimurium,* or *Agrobacterium tumefaciens*, and most preferably the transporter derived from *Salmonella typhimurim*.

Preferably, in the present invention, the myo-inositol transporter may be one or more transporters selected from a group consisting of proteins having an amino acid sequence disclosed in SEQ ID NOS: 1 to 6.

The term "inositol dehydrogenase" used in the present specification is an enzyme having an activity of catalyzing a chemical reaction, in which myo-inositol is converted into 2-keto-myo-inositol by means of NAD dependent oxidation as shown in the Reaction Equation 1 below, or catalyzing an inverse reaction thereof. In the present specification, "inositol dehydrogenase" is also described as its coding gene name "iolG."

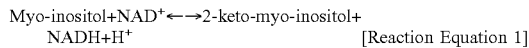

[Reaction Equation 1]

It is reported that inositol dehydrogenase has been separated from *Aerobacter aerogenes* (Berman T, Magasanik B (1966). J. Biol. Chem. 241 (4): 800-806; LARNER J, JACKSON W T, GRAVES D J, STAMER J R (1956). Arch. Biochem. Biophys. 60 (2): 352-363) and yeast *Cryptococcus melibiosum* (Vidal-Leiria M, van Uden N (1973). Biochim. Biophys. Acta. 293 (2): 295-303).

Inositol dehydrogenase, which can be used in the present invention, is the one derived from *Agrobacterium tumefaciens, Bacillus subtilis, Corynebacterium glutamicum*, or *Pantoea ananantis*. More preferably, inositol dehydrogenase in the present invention may be any one selected from a group consisting of proteins having an amino acid sequence disclosed in SEQ ID NOS: 21, 23, 25, 27, 29 and 31.

In the present invention, the term "inosose isomerase" is an enzyme having an activity of catalyzing an isomerization reaction, in which 2-keto-myo-inositol is converted into 1-keto-D-chiro-inositojl as shown in the Reaction Equation 2 below, or catalyzing an inverse reaction thereof. In the present invention, "inosose isomerase" is also described as its coding gene name "ioll."

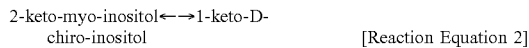

[Reaction Equation 2]

Inosose isomerase, which can be used in the present invention, is the one separated from *Agrobacterium tumefaciens, Bacillus subtilis, Corynebacterium glutamicum* or *Pantoea ananantis*. More preferably, inosose isomerase in the present invention can be any one selected from a group consisting of proteins having an amino acid sequence disclosed in SEQ ID NOS: 22, 24, 26, 28 and 30.

1-keto-D-chiro-inositol generated by means of the Reaction Equation 2 above generates D-chiro-inositol, which is a final product of the present invention by means of the Reaction Equation 3 below. In the Reaction Equation 3 below, a reaction is catalyzed by "inositol dehydrogenase," the enzyme described above.

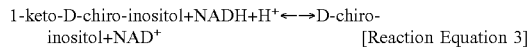

[Reaction Equation 3]

In the present invention, myo-inositol is converted into D-chiro-inositol in a host cell by means of a continuous reaction of the Reaction Equations 1 to 3. As described above, the reaction of the Reaction Equations 1 and 3 is catalyzed by "inositol dehydrogenase" and the reaction of the Reaction Equation 2 is catalyzed by "inosose isomerase."

In the present invention, a myo-inositol transporter, inositol dehydrogenase, and inosose isomerase coding DNA sequence is operatively linked to a promoter within a recombinant vector.

In the present specification, the term "operatively linked" means to be functionally linked with an expression control sequence of a DNA sequence, so that the expression of the DNA sequence is controlled by the expression control sequence.

In the present specification, the term "promoter" means a DNA sequence that can control the expression of the coding sequence of the gene or the functional RNA.

In the present invention, a vector can be constructed through various methods known in the related art, and the detailed method thereof is disclosed in "Molecular Cloning, A Laboratory Manual" (Cold Spring Harbor Laboratory Press, 2001) by Sambrook et al. and this document is inserted herein by reference.

In the present invention, a recombinant vector can be constructed as a vector for cloning or expression, and also can be constructed in such a way that a procaryotic cell or a eukaryotic cell is a host.

For example, if a vector in the present invention is an expression vector and a procaryotic cell is a host, it is common to include a strong promoter (e.g. pL λ promoter, trp promoter, lac promoter, T7 promoter, tac promoter, etc.) capable of doing transcription, a ribosome-binding site for the start of translation, and a transcription/translation termination sequence. If *Escherichia coli* (*E. coli*) is used as a host cell, a promoter and operator region in an *E. coli* tryptophan biosynthetic pathway (Yanofsky, C., J. Bacteriol., 158:1018-1024(1984)) and a leftward promoter of phage λ (pL λ promoter, Herskowitz, I. and Hagen, D., Ann. Rev. Genet., 14:399-445(1980)) can be used as a control region.

In the present invention, the vector may include as a selection marker an antibiotic resistance gene commonly used in the art. For example, there is a resistance gene to ampicillin, gentamycin, carbenicillin, chloramphenicol, streptomycin, kanamycin, geneticin, neomycin and tetracycline, but is not limited thereto. The antibiotic resistance gene above is operatively linked to a promoter for expression thereof.

The vector, which can be used in the present invention, can be prepared by manipulating plasmid, which is often used in the art (e.g. pSC101, ColE1, pBR322, pUC8/9, pHC79, pGEX series, pET series, pUC19 and the like), phage (e.g. λ gt4 o λ B, λ-Charon, λ Δz1, M13 and the like) or virus, (e.g. SV40 and the like)

In the present invention, the vector is preferably a vector for a procaryotic cell and includes a nucleic acid sequence capable of doing replication in a procaryotic host cell, especially in *E. coli*. Therefore, the vector herein can include a replication origin of bacteria of colA, colE1 or p15A, or a replication origin of bacteriophage such as f1 origin.

A host cell, which is capable of stably and continuously cloning and expressing a recombinant vector of the present invention, can be any host cell known in the art. For example, the host cell may be a eukaryotic cell or a procaryotic cell such as a mammalian cell, an insect cell and yeast, but preferably a procaryotic cell. As for the procaryotic cell, for example, there are *E. coli* such as *E. coli* JM109, *E. coli* BL21, *E. coli* RR1, *E. coli* LE392, *E. coli* B, *E. coli* X 1776 and *E. coli* W3110, a *bacillus* sp. strain such as *bacillus subtilis* and *bacillus thuringiensis*, and intestinal bacteria and strains such as *Salmonella typhimurium, Serratia marcescens, Corynebacterium glutamicum* and various *Pseudomonas* species.

If a host cell is a procaryotic cell, a method for transporting the vector of the present invention into a host cell can be carried out by means of a CaCl$_2$ method (Cohen, S. N. et al., Proc. Natl, Acac. Sci. USA, 9:2110-2114(1973)), a Hanahan method (Cohen, S. N. et al., Proc. Natl, Acac. Sci. USA, 9:2110-2114(1973); and Hanahan, D., J. Mol. Biol., 166: 557-580(1983)) and an electroporation method (Dower, W. J. et. al., Nucleic. Acids Res., 16:6127-6145(1988).

(b): Culturing a Transformed Host Cell in a Medium Including Myo-Inositol

While the transformed host cell is being cultivated, a myo-inositol transporter, inositol dehydrogenase and inosose isomerase in a recombinant expression vector are expressed, and the myo-inositol in a culture fluid is absorbed into a cell and converted into D-chiro-inositol by means of catalysis of the enzymes above.

The cultivation of the transformed host cell can be performed by means of a known method for cultivating a host cell or a modified method thereof. For example, if a host cell is E. coli, a medium for cultivating the transformed host cell can be a natural medium or a synthetic medium, as long as the medium includes a carbon source, a nitrogen source, inorganic salt and the like. A carbon source available includes: carbohydrate such as glucose, fructose and sucrose; starch and hydrolysate thereof; acetic acid and organic acid such as propionic acid; alcohol such as ethanol, propanol and glycerol, and the like. A nitrogen source includes: ammonia; ammonium salt of inorganic acid or organic acid such as ammonium chloride, ammonium sulfate, ammonium acetate and ammonium phosphate; peptone, meat extract, yeast extract, corn steep liquor, casein hydrolysate, soybean extract and soybean hydrolysate; and a variety of fermented cells, resolvents and the like. An inorganic salt includes potassium dihydrogen phosphate, dipotassium hydrogen phosphate, magnesium phosphate, magnesium sulfate, sodium chloride, manganese sulfate, copper sulfate, calcium carbonate, and the like.

Culture is generally performed under an aerobic condition such as a shaking culture or rotation by a rotating machine. A culture temperature is preferably performed in a range of 10° C. to 40° C., and a culture time is generally performed for five hours to seven days. A medium pH is preferably maintained in a range of 3.0 to 9.0. The medium pH may be controlled with inorganic or organic acid, alkaline solution, urea, calcium carbonate, ammonia and the like. During culture, it is possible to add antibiotics such as ampicillin, streptomycin, chloramphenicol, kanamycin and tetracyclin for the preservation and expression of a recombinant vector, if necessary. In case of culturing the transformed host cell with the recombinant expression vector having an inducible promoter, it is possible to add an inducer suitable for a medium, if necessary. For example, if the expression vector contains a lac promoter, it is possible to add isopropyl-3-D-thiogalactopyranoside (IPTG) therein. If the expression vector contains a trp promoter, it is possible to add indoleacrylic acid therein.

According to a preferred embodiment of the present invention, a method of the present invention further includes (c) separating D-chiro-inositol from a culture product of the transformed host cell after the step (b).

(c): Separating D-Chiro-Inositol from a Culture Product of the Host Cell

The separation of D-chiro-inositol from a culture fluid where a transformed host cell is cultured is performed by using a known method for separating and refining carbohydrate or sugar and a modified method thereof.

If D-chiro-inositol exists in a state that it is dissolved in a medium, a transformant cultured from the medium is removed. For example, the cultured transformant is removed from the culture fluid by means of centrifugation, microfiltration or the like, so as to obtain culture supernatant only. A method for obtaining D-chiro-inositol from culture supernatant can be a known method for separating and refining sugar in the related art and a modified method thereof.

The known method for separating and refining sugar in the related art includes a separation method by selective adsorption using a zeolite molecular sieve (U.S. Pat. No. 4,482,761), a separation method by column chromatography using a cation exchange resin (U.S. Pat. No. 5,096,594), a separation method by column chromatography using an anion exchange resin (U.S. Pat. No. 5,482,631), a method of absorption by activated carbon and elution by organic solvent (Korea Patent No. 10-0753982), a freeze-drying and recrystallizing method, and the like. These methods, modified methods thereof and combinations thereof can be used, but not limited thereto.

According to another aspect of the present invention, the present invention provides a transformed host cell with a recombinant vector, the recombinant vector including: (i) a myo-inositol transporter coding DNA sequence operatively linked to a promoter; and (ii) an inositol dehydrogenase coding DNA sequence and an inosose isomerase coding DNA sequence operatively linked to a promoter.

According to yet another aspect of the present invention, the present invention provides a composition for preparing D-chiro-inositol from myo-inositol including the above-mentioned transformed host cell.

According to still yet another aspect of the present invention, the present invention provides a recombinant vector kit for preparing D-chiro-inositol from myo-inositol, including (i) a recombinant vector including a myo-inositol transporter coding DNA sequence operatively linked to a promoter; and (ii) a recombinant vector including an inositol dehydrogenase coding DNA sequence and an inosose isomerase coding DNA sequence operatively linked to a promoter as an active component.

In a kit including a host cell, a composition and a recombinant vector including the host cell according to another exemplary embodiment of the present invention, the contents about the myo-inositol transporter, inositol dehydrogenase and inosose isomerase; a recombinant expression vector including a DNA sequence coding therefor; and the host cell including the recombinant expression vector, is the same as the contents of the exemplary embodiment of the present invention mentioned above, so the repeated description will be omitted here.

ADVANTAGEOUS EFFECTS

The present invention relates to a method for preparing D-chiro-inositol from myo-inositol by using a transformed host cell, which expresses the enzyme myo-inositol transporter, inositol dehydrogenase, and inosose isomerase. According to the method of the present invention, myo-inositol can be converted into D-chiro-inositol.

BRIEF DESCRIPTION OF THE DRAWINGS

in FIG. 6b. o: microbe growth, ●: pH and ▲: amount of remaining glycerol at the temperature of 37° C. in FIG. 6c.

Best Mode

Figure 1:
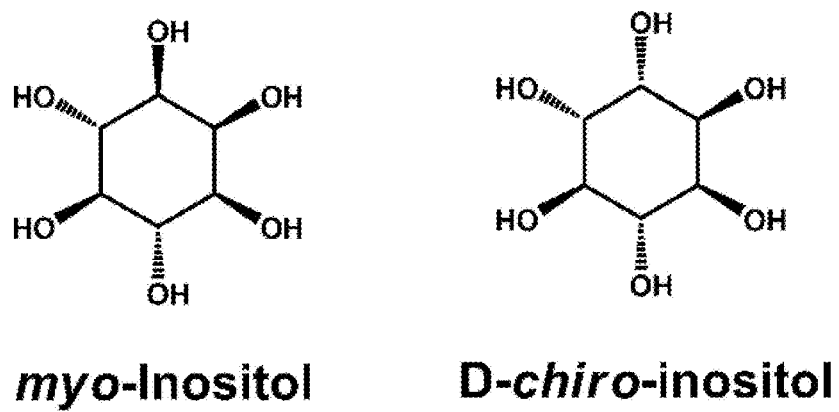
FIG. 1 shows a chemical structure of myo-inositol and D-chiro-inositol.

Hereinafter, the present invention will be described in detail in light of the following exemplary embodiments. While those exemplary embodiments are intended to describe the present invention more clearly, it would be obvious to those skilled in the art that they are not used to limit the range of the present invention disclosed in the claims.

Exemplary Embodiment

Exemplary Embodiment 1: Cloning of Myo-Inositol Transporter Gene and Preparation of a Recombinant Vector Including the Same Each of major and minor genes of a myo-inositol transporter was cloned from *Bacillus subtilis, Salmonella typh-* *imurium* or *Agrobacterium tumefaciens* strains, which are reported to use myo-inositol as a carbon source.

In case of *B. subtilis*, a myo-inositol transporter gene is an iolT gene and an iolF gene. In case of *S. typhimurium*, a myo-inositol transporter gene is an iolT 1 gene and an iolT2 gene. In case of *A. tumefaciens*, a myo-inositol transporter gene is an Atu5935 gene and an Atu2525 gene. Information on the genes above is as shown in Table 1.

TABLE 1

| Strain | Gene | SEQ ID NO: | Genbank Accession No. (GI, NID, PID) |
|---|---|---|---|
| *B. subtilis* | BsioIT | SEQ ID NO: 1 | BSU06230, GI: 2632936 |
|  | BsioIF | SEQ ID NO: 2 | BSU39710, GI: 225185479 |
| *S. typhimurium* | StioIT1 | SEQ ID NO: 3 | STM4418, GI16422981 |
|  | StioIT2 | SEQ ID NO: 4 | SMT4419, GI: 16422982 |
| *A. tumefaciens* | Atu5935 | SEQ ID NO: 5 | Atu5935, G1: 16119622 |
|  | Atu2525 | SEQ ID NO: 6 | Atu2525, GI: 15889790 |

1-1. Preparation of Recombinant Vector pACYCD-BsiolT (F2) and pACYCD-BsiolT-BsiolF(F2)

In case of *B. subtilis* strain, a major transporter iolT and a minor transporter iolF are introduced from a genome DNA of *Bacillus subtilis* subsp. *subtilis*_str. 168 (taxid:224308; GenBank NID: NC_000964, ATCC23857) into a pACYC-Duet-1 expression vector, so that pACYCD-BsiolT(F2) and pACYCD-BsiolT-BsiolF(F2) is constructed. To describe in detail, iolT is amplified by using primer BsiolT-F2 and BsiolT-R from the genome DNA of *B. subtilis*, cut off with restriction enzymes SacI and BamHI, and inserted into the same region of vector pACYDuet-1 (Novagen), so that pACYCD-BsiolT(F2) is prepared. Also, iolF is amplified by using primer BsiolF-F and BsiolF-R, cut off with restriction enzymes NdeI and SaiI, and inserted into the NdeI and XhoI regions of the pACYCD-BsiolT(F2) prepared above, so that pACYCD-BsiolT-BsiolF(F2) is prepared.

1-2. Preparation of Recombinant Vector pACYCD-StiolT1(F2) and pACYCD-StiolH-StiolT2(F2)

In case of *S. typhimurium* strain, iolT 1, known as a major transporter, and iolT2, known as a minor transporter, are amplified from *Salmonella enterica* subsp. *enterica* serovar Typhimurium str. LT2 ATCC700720 (taxid:99287; GenBank NID: NC_006511, ATCC700720), introduced into pACYC-Duet-1 expression vector, so that pACYCD-StiolH (F2) and pACYCD-StiolT1-StiolT2(F2) is constructed. To describe in detail, iolT 1 is amplified from the genome DNA of *S. typhimurium* by using primer StiolT 1-F2 and StiolT 1-R, cut off with restriction enzymes NcoI and BamHI, and inserted into the same region of pACYDuet-1 vector, so that pACYCD-StiolT1 (F2) is prepared. Also, iolT2 is amplified by using primer StiolT2-F and StiolT2-R, cut off with restriction enzymes NdeI and SaiI, and inserted into the NdeI and XhoI regions of the pACYCD-StiolT 1 (F2) prepared above, so that pACYCD-StiolT1-StiolT2(F2) is prepared.

1-3. Preparation of Recombinant Vector pACYCD-Atu5935(F2) and pACYCD-Atu5935-Atu2525(F2)

In case of *A. tumefaciens*, Atu5935 is amplified from the genome DNA of *Agrobacterium tumefaciens* str. C58 (taxid: 176299; GenBank NID: NC_003062, ATCC33970) by using primer Atu5935-F2 and Atu5935-R, cut off with restriction enzymes NcoI and BamHI, and inserted into the same region of pACYCDuet-1 vector, so that pACYCD-Atu5935(F2) is prepared. Also, Atu2525 is amplified by using primer Atu2525-F and Atu2525-R, cut off with restriction enzymes NdeI and SaiI, and inserted into the NdeI and XhoI regions of the pACYCD-Atu2525(F2) prepared above, so that pACYCD-Atu5935-Atu2525(F2) is prepared.

1-4. Preparation of Recombinant Vector pCOLAD-sAtiep-sAtiepf

To evaluate the activity of the cloned myo-inositol transporter, an inositol dehydrogenase gene (iolG) and an inosose isomerase gene (ioII), which convert myo-inositol into D-chiro-inositol, are cloned from *A. tumefaciens* and introduced into vector pCOLADuet-1 (Novagen), so that a recombinant plasmid vector pCOLAD-sAtiep-sAtiepf is prepared. To describe in more detail, DNA synthesis [GenScript Inc., 860 Centennial Ave., Piscataway, N.J. 08854, USA] is performed based on amino acid sequences of BD171257_CDS1 and CDS2 of *Agrobacterium* sp. AB10121 (W002/055715A), so that a synthesized DNA molecule sAtiep (SQ ID No. 50) and a synthesized DNA molecule sAtiepf (SQ ID No. 51) is prepared respectively. The synthesized DNA molecule sAtiep, as a template, is PCR-amplified by using primer sAtiep-TF and sAtiep-TR, cut off with restriction enzymes BspHI and SacI, and inserted into the same restriction enzyme region of pCOLADuet-1, so that pCOLAD-sAtiep is prepared. Then, the synthesized DNA molecule sAtiepf is cut off with NdeI and SaiI, and inserted into the NdeI and XhoI regions of the prepared vector pCOLAD-sAtiep, so that a recombinant vector pCOLAD-sAtiep-sAtiepf is prepared finally.

The primers used for preparing the recombinant vector are summarized in Table 2, and information on the prepared recombinant vectors and sequences related thereto is summarized in Table 3.

TABLE 2

| Primer | SEQ ID NO: | Restriction enzyme region |
|---|---|---|
| BsioIT-F2 | SEQ ID NO: 7 | SacI |
| BsioIT-R | SEQ ID NO: 8 | BamHI |
| BsioIF-F | SEQ ID NO: 9 | BamHI-NdeI |
| BsioIF-R | SEQ ID NO: 10 | SaiI |
| StioIT1-F2 | SEQ ID NO: 11 | EcoRI-NcoI |
| StioIT1-R | SEQ ID NO: 12 | BamHI |
| StioIT2-F | SEQ ID NO: 13 | BamHI-NdeI |
| StioIT2-R | SEQ ID NO: 14 | SaiI |
| Atu5935-F2 | SEQ ID NO: 15 | EcoRI-NcoI |
| Atu5935-R | SEQ ID NO: 16 | BamHI |
| Atu2525-F | SEQ ID NO: 17 | BamHI-NdeI |
| Atu2525-R | SEQ ID NO: 18 | SaiI |
| sAtiep-TF | SEQ ID NO: 19 | BspHI |
| sAtiep-TR | SEQ ID NO: 20 | SacI |

TABLE 3

| Vector, Recombinant Vector, Gene | Genbank Accession No. (GI, NID, PID) or References |
|---|---|
| pACYDuet-1 | Novagen |
| pACYCD-BsioIT(F2) | The present invention |
| pACYCD-BsioIT-BsioIF(F2) | The present invention |
| pACYCD-StioIT1(F2) | The present invention |
| pACYCD-StioIT1-StioIT2(F2) | The present invention |
| pACYCD-Atu5935(F2) | The present invention |
| pACYCD-Atu5935-Atu2525(F2) | The present invention |
| BD171257-CDS1 | BD171257 or GI: 27877069 |
| BD171257-CDS2 | BD171257 or GI: 27877069 |
| sAtiep | GenScript Inc. |
| sAtiepf | GenScript Inc. (containing restriction enzymes NdeI and SaiI) |
| pCOLADuet-1 | Novagen |
| pCOLAD-sAtiep-sAtiepf | The present invention |

Exemplary Embodiment 2: Evaluation of the Activity of Myo-Inositol Transporter

As prepared in the Exemplary Embodiment 1 above, each recombinant plasmid containing a myo-inositol transporter derived from *B. subtilis*, *S. typhimurium* and *A. tumefaciens*, pACYCD-BsioIT(F2), pACYCD-BsioIT-BsioIF(F2), pACYCD-StioIT 1 (F2), pACYCD-StioIT 1-StioIT2(F2), pACYCD-Atu5935(F2) and pACYCD-Atu5935-Atu2525 (F2), are transformed in *E. coli* BL21(DE3) along with a recombinant plasmid pCOLAD-sAtiep-sAtiepf including inositol dehydrogenase and inosose isomerase coding genes, which convert from myo-inositol to D-chiro-inositol, so that a transformed strain is prepared.

Figure 2:
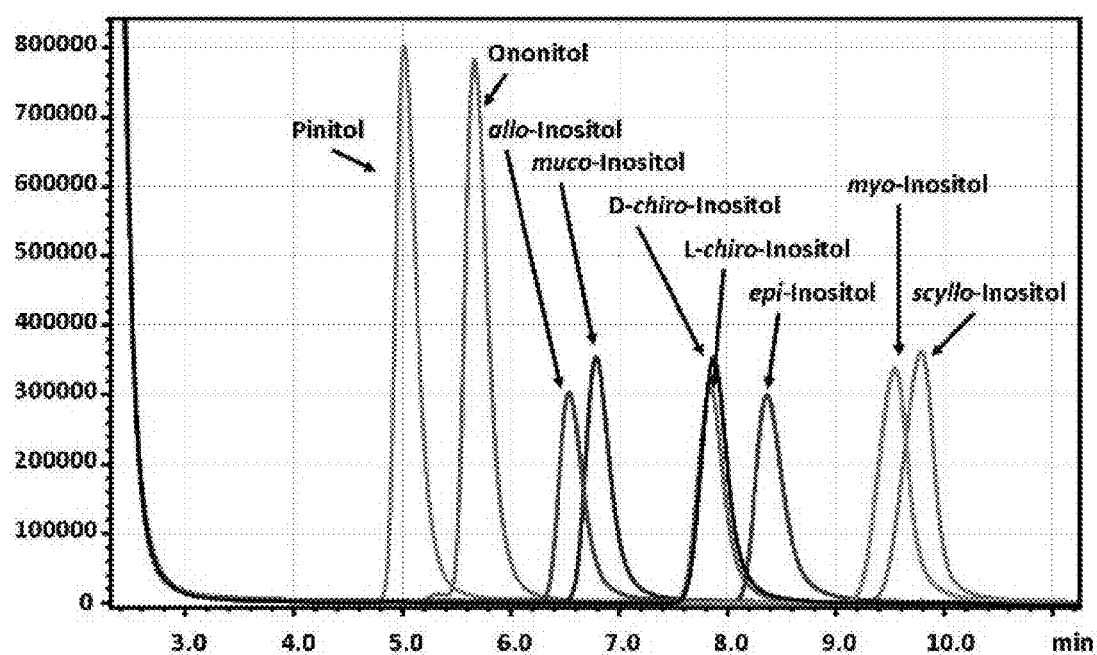
FIG. 2 shows an HPLC chromatogram on myo-inositol, D-chiro-inositol and a stereoisomer or derivatives thereof.

A 5 mL of the recombinant transformed strain prepared above is cultured in a glass test tube having 25 mm in diameter and 150 mm in height. When it comes to culture conditions, when a microbe reaches OD 0.6 under the conditions of 30° C. and 250 rpm by using an M9 minimum medium containing 1% (w/v) myo-inositol, 50 mg/L of chloramphenicol and 50 mg/L of kanamycin, 1 mM of IPTG is added to perform induction, and cultured for 48 hours. For the analysis of myo-inositol and D-chiro-inositol, a culture fluid is put into centrifugation, a 1 mL of culture supernatant thereof is taken out, boiled for 10 minutes, put into centrifugation again, and a 500 uL of supernatant thereof is taken out. The pre-treated culture supernatant is analyzed with HPLC (Shimadzu LCIOAvp) by using an RI detector under the conditions of Kromasil 5NH2 column (4.6 mm×250 mm), mobile phase 75% acetonitrile and column temperature 40° C. The HPLC chromatogram of myo-inositol, D-chiro-inositol and isomers thereof are shown in FIG. 2.

Figure 3:
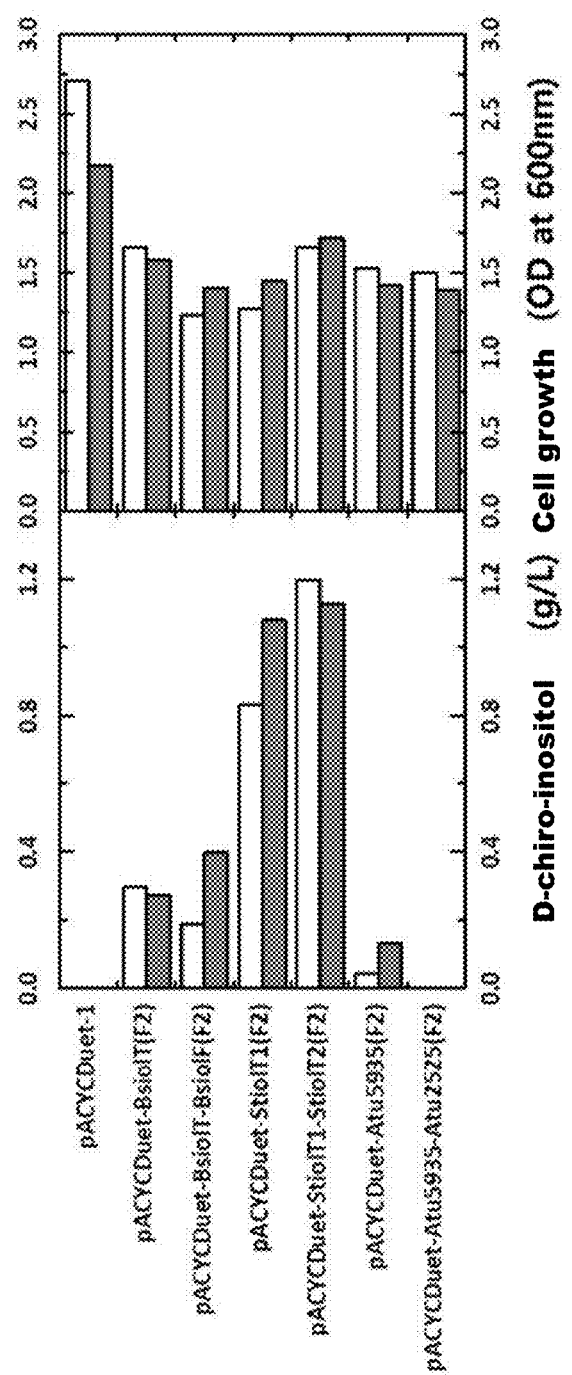
FIG. 3 shows results of measuring a conversion ratio of D-chiro-inositol from myo-inositol and a bacterial growth rate in a transformed E. coli obtained by additionally introducing an inositol transporter of various origins to E. coli, which expresses myo-inositol dehydrogenase and inosose isomerase. Each test group for inositor transporter shows a result from culturing for 24 and 48 hours recombinant *E. coli* prepared by introducing a transporter expression vector along with pCOLAD-sAtiep-sAtiepf. A white rod indicates a value measured after culturing for 24 hours, while a gray rod represents a value measured after culturing for 48 hours.
Figure 4:
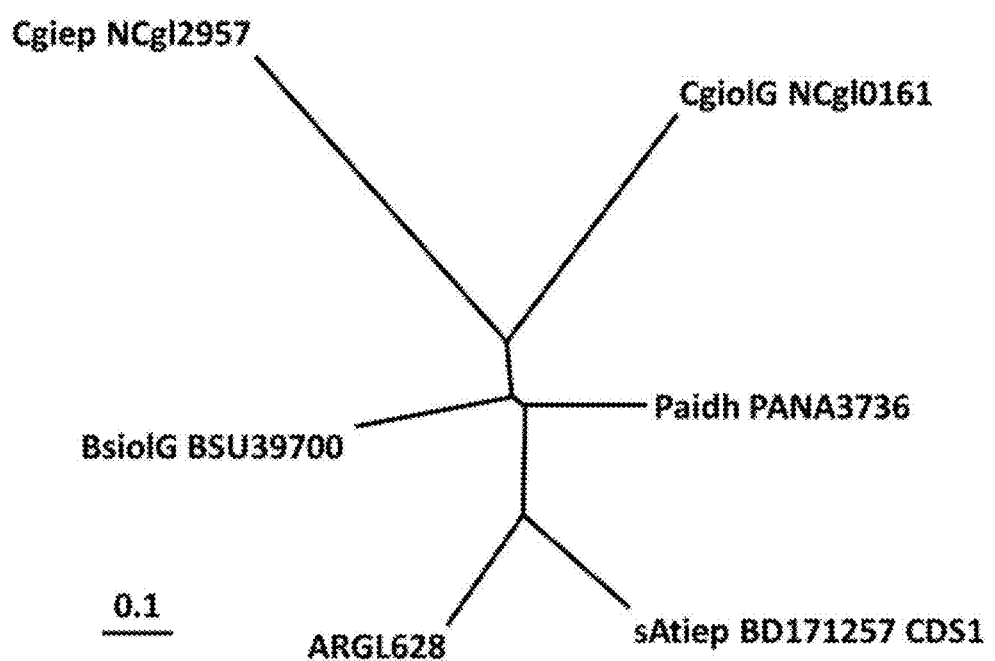
FIG. 4 shows a phylogenetic tree by homology analysis of myo-inositol dehydrogenase (iolG).
Figure 5:
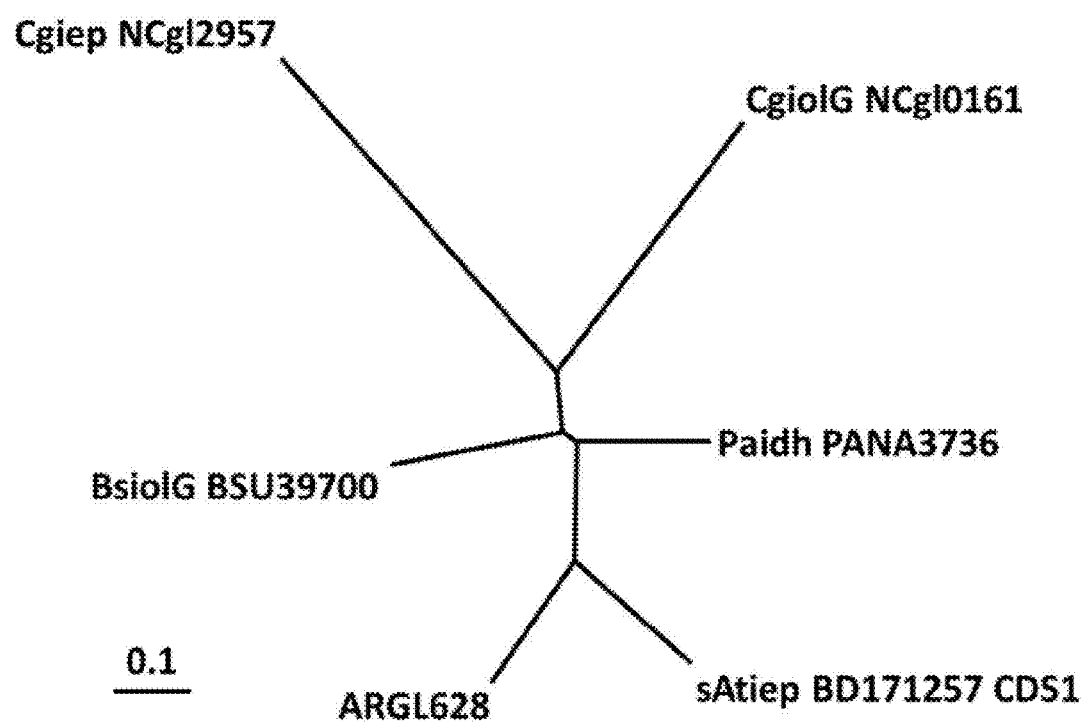
FIG. 5 shows a phylogenetic tree by homology analysis of inosose isomerase (iolI).

The results of measuring the activity of each myo-inositol transporter are shown in FIG. 3. According to the results of FIG. 3, in case of pACYCD-StioIT1-StioIT2 containing both major and minor transporters StioIT 1 and StioIT2 derived from *S. typhimurium* in pACYCDuet-1, a conversion ratio of D-chiro-inositol is best. In the myo-inositol transporter derived from *B. subtilis* and *A. tumefaciens*, a conversion ratio of D-chiro-inositol is lowest. In case of *S. typhimurium* transporter having the best conversion ratio, about 1.2 g/L of D-chiro-inositol is converted from 10 g/L myo-inositol in 24 hours, while about 1.1 g of D-chiro-inositol is converted in 48 hours. Therefore, it is found that a conversion ratio does not increase in 24 hours later. When a gene is introduced, a microbe growth appears to slightly slow down. That's probably because it is located on a cell membrane due to the characteristics of transporter protein, thus exhibiting toxicity upon over-expression.

Exemplary Embodiment 3: Cloning of Inositol Dehydrogenase and Inosose Isomerase Genes and Preparation of a Recombinant Vector Including the Same Through continuous responses of Reaction Equations 1 to 3 below, D-chiro-inositol is converted from myo-inositol. The reactions of Reaction Equations 1 and 3 are catalyzed by inositol dehydrogenase and the reaction of Reaction Equation 2 is catalyzed by inosose isomerase.

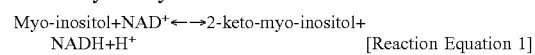

Myo-inositol+NAD$^+$ ↔ 2-keto-myo-inositol+ NADH+H$^+$  [Reaction Equation 1]

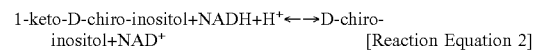

1-keto-D-chiro-inositol+NADH+H$^+$ ↔ D-chiro-inositol+NAD$^+$  [Reaction Equation 2]

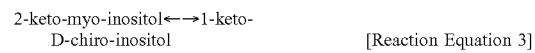

2-keto-myo-inositol ↔ 1-keto-D-chiro-inositol  [Reaction Equation 3]

A gene having the same function as inositol dehydrogenase gene (iolG) and inosose isomerase gene (ioll) is cloned from *A. tumefaciens, B. subtilis, Corynebacterium glutamicum* and *Pantoea ananatis*. Genes corresponding to iolG and ioll genes are amplified from a genome DNA of the strains above, a pair and a combination of the amplified iolG and ioll genes are inserted into pCOLADuet-1 expression vector (Novagen), so that six kinds of recombinant plasmid are prepared. Information on the iolG and ioll homologous genes listed above is shown in Table 4 below.

TABLE 4

| Strain | Gene | SEQ ID NO: | Genbank Accession No. (GI, NID, PID) or References |
|---|---|---|---|
| *A. tumefaciens* | sAtiep | SEQ ID NO: 21 | BD171257_CDS1 or GI: 27877069 |
| | sAtiepf | SEQ ID NO: 22 | BD171257_CDS2 or GI: 27877069 |
| | AGRL628 | SEQ ID NO: 23 | AGR_L_628, GI: 159186216 |
| | AGRL627 | SEQ ID NO: 24 | AGR_L_627, GI: 159186217 |
| *B. subtilis* | BsiolG | SEQ ID NO: 25 | BSU39700, GI: 255767850 |
| | BsiolI | SEQ ID NO: 26 | BSU39680, G1: 16081019 |
| *C. glutamicum* | CgiolG | SEQ ID NO: 27 | NCg10161 or GI: 19551414 |
| | CgiolI0169 | SEQ ID NO: 28 | NCg10169 or GI: 19551422 |
| *P. ananatis* | Paidh | SEQ ID NO: 29 | PANA_3736, GI: 291619289 |
| | PaiolI | SEQ ID NO: 30 | PANA_3268, GI: 291618821 |
| *C. glutamicum* | Cgiep | SEQ ID NO: 31 | NCgI2957 or GI: 19554252 |

3-1. Preparation of Recombinant Vector pCOLAD-sAtiep-sAtiepf

A method for preparing recombinant vector pCOLAD-sAtiep-sAtiepf including iolG and ioll genes from *Agrobacterium* sp. AB10121 strain (WO 02/055715A).

3-2. Preparation of Recombinant Vector pCOLAD-AGRL628-AGRL627

A recombinant vector including iolG and ioll genes derived from *A. tumefaciens* is prepared through the following method. An AGRL628 gene corresponding to iolG is amplified from a genome DNA of *Agrobacterium tumefaciens* str. C58(taxid:176299; GenBank NID:NC_003062, ATCC33970) by using primer AGRL628-F and AGRL628-R. Then, the resulting one is cut off with restriction enzymes Pcil and SacI, and introduced into the Ncol and SacI regions of pCOLADuet-1 (Novagen), so that pCOLAD-AGRL628 is prepared. Also, AGRL_627 corresponding to ioll is amplified by using AGRL627-F and AGRL627-R primer. Then, the resulting one is cut off with restriction enzymes Ndel and SaiI, and inserted into the Ndel and Xhol regions of pCOLAD-AGRL628, so that pCOLAD-AGRL628-AGRL627 recombinant vector is prepared.

3-3. Preparation of Recombinant Vector pCOLAD-BsiolG-BsiolI

A recombinant vector including iolG and ioll genes derived from *B. subtilis* is prepared through the following method. BsiolG corresponding to iolG is amplified from a genome DNA of *Bacillus subtilis* subsp. *subtilis* str. 168 (taxid:224308; GenBank NID:NC_000964, ATCC23857) by using BsiolG-F and BsiolG-R primer. Then, the resulting one is cut off with restriction enzymes Pcil and Notl, and inserted into the Ncol and Notl regions of pCOLADuet-1, so that pCOLAD-BsiolG is prepared. Also, BsiolI corresponding to ioll is amplified by using BsiolI-F and BsiolI-R primer. Then, the resulting one is processed with restriction enzymes Ndel and PacI, and inserted into the same restriction enzyme region of the plasmid pCOLAD-BsiolG constructed above, so that pCOLAD-BsiolG-BsiolI is prepared.

3-4. Preparation of Recombinant Vector pCOLAD-CgiolG-CgiolI0169

A recombinant vector including iolG and ioll genes derived from *C. glutamicum* is prepared through the following method. CgiolG corresponding to iolG is amplified from a genome DNA of *Corynebacterium glutamicum* ATCC 13032 (taxid:196627; GenBank NID:NC_003450, ATCC13032) by using CgiolG-F and CgiolG-R primer, cut off with restriction enzymes BspHl and Notl, and inserted into the Ncol and Notl regions of pCOLADuet-1, so that pCOLAD-CgiolG is prepared. Also, CgiolI0169 corresponding to ioll is amplified by using CgiolI0169-F and CgiolI0169-R primer. Then, the resulting one is processed with Ndel and Pacl, and inserted into the same restriction enzyme region of the pCOLAD-CgiolG constructed above, so that pCOLAD-CgiolG-CgiolI0169 vector is prepared.

3-5. Preparation of Recombinant Vector pCOLAD-Paidh-PaiolI

A recombinant vector including iolG and ioll genes derived from *Pantoea ananatis* is prepared through the following method. Paidh corresponding to iolG is amplified from a genome DNA of *Pantoea ananatis* LMG 20103 (taxid:706191; GenBank NID:NC_013956, KCCM40419) by using Paidh-F and Paidh-R primer, cut off with restriction enzymes Pcil and Notl, and inserted into the Ncol and Notl regions of pCOLADuet-1, so that pCOLAD-Paidh is prepared. Also, PaiolI corresponding to ioll is amplified by using PaiolI-F and PaiolI-R primer. Then, the resulting one is processed with Ndel and Pacl, and inserted into the same restriction enzyme region of the pCOLAD-Paidh prepared above, so that pCOLAD-Paidh-PaiolI is prepared.

3-6. Preparation of Recombinant Vector pCOLAD-Cgiep-PaiolI

To prepare a recombinant vector in combination of iolG and ioll genes derived from different strains, first of all, an iolG homologous gene Cgiep (NCg12957 or G1:19554252) whose function has not been reported and which is less homogenous with BD171257_CDS 1 (GI:27877069), which is an iolG gene on the *C. glutamicum* genome, is cloned. Also, in case of a corresponding ioll gene, PaiolI, which is ioll derived from *P. ananatis* whose function has not been reported and which is less homogenous with BD171257_CDS 2(GI:27877069), which is also an ioll gene, is used in combination. To describe in more detail, Cgiep is amplified from a genome DNA of *Corynebacterium glutamicum* ATCC 13032 (taxid:196627; Gen Bank NID: NC_003450, ATCC13032) by using primer Cgiep-F and Cgiep-R, processed and cut off with restriction enzymes BspHl and Notl, and inserted into the Ncol and Notl regions of the pCOLADuet-1, so that pCOLAD-Cgiep is prepared. Then, pCOLAD-Cgiep is processed and cut off with Ndel and PacI, and PaioII, which is cut off with the same restriction enzyme, is inserted therein, so that pCOLAD-Cgiep-PaioII vector is finally prepared.

In the Exemplary Embodiment 3, the primer used for preparing the recombinant vector is shown in the Table 5 below, and the recombinant vector prepared above is shown in the Table 6.

TABLE 5

| Primer | SEQ ID NO: | Restriction enzyme region |
| --- | --- | --- |
| AGRL628-F | SEQ ID NO: 32 | PciI |
| AGRL628-R | SEQ ID NO: 33 | SacI |
| AGRL627-F | SEQ ID NO: 34 | BamHI-NdeI |
| AGRL627-R | SEQ ID NO: 35 | SaiI |
| BsioIG-F | SEQ ID NO: 36 | PciI |
| BsioIG-R | SEQ ID NO: 37 | NotI |
| BsioII-F | SEQ ID NO: 38 | NdeI |
| BsioII-R | SEQ ID NO: 39 | PacI |
| CgioIG-F | SEQ ID NO: 40 | BspHI |
| CgioIG-R | SEQ ID NO: 41 | NotI |
| CgioII0169-F | SEQ ID NO: 42 | NdeI |
| CgioII0169-R | SEQ ID NO: 43 | PacI |
| Paidh-F | SEQ ID NO: 44 | PciI |
| Paidh-R | SEQ ID NO: 45 | NotI |
| PaioII-F | SEQ ID NO: 46 | NdeI |

TABLE 5-continued

| Primer | SEQ ID NO: | Restriction enzyme region |
| --- | --- | --- |
| PaioII-R | SEQ ID NO: 47 | PacI |
| Cgiep-F | SEQ ID NO: 48 | BspHI |
| Cgiep-R | SEQ ID NO: 49 | NotI |

TABLE 6

| Vector and Recombinant Vector | Genbank Accession No. (GI, NID, PID) or References |
| --- | --- |
| pCOLADuet-1 | Novagen |
| pCOLAD-sAtiep-sAtiepf | The present invention |
| pCOLAD-AGRL628-AGRL627 | The present invention |
| pCOLAD-BsioIG-BsioII | The present invention |
| pCOLAD-CgioIG-CgioII0169 | The present invention |
| pCOLAD-Paidh-PaioII | The present invention |
| pCOLAD-Cgiep-PaioII | The present invention |

3-7. Homology of Cloned Genes

A phylogenetic tree of the cloned inositol dehydrogenase (iolG) and inosose isomerase (iolI) genes is shown in the Tables 4 and 5, and the results of analyzing the homology of those genes are shown in the Tables 7 and 8.

TABLE 7

| Gene | SEQ ID NO: | Homology (%) of amino acid sequence of SEQ ID NO: 21 | Genbank Accession No. (NID, PID, GI) | Reference |
| --- | --- | --- | --- | --- |
| sAtiep | SEQ ID NO: 21 | 100 | BD171257 CDS-1, G 1: 27877069 | JP2001-006878, W002055715A1 |
| AGRL628 | SEQ ID NO: 23 | 90.5 | AGR_L_628, GI: 159186216 | |
| Paidh | SEQ ID NO: 29 | 56.8 | PANA_3736, GI: 291619289 | |
| BsioIG | SEQ ID NO: 25 | 50.4 | BSU39700, GI: 255767850 | Yoshida et al. (AEM72, 2006) |
| CgioIG | SEQ ID NO: 27 | 35.4 | NCgl0161, G1: 19551414 | |
| Cgiep | SEQ ID NO: 31 | 21.7 | NCgl2957, GI: 19554252 | |

TABLE 8

| Gene | SEQ ID NO: | Homology (%) of amino acid sequence of SEQ ID NO: 21 | Genbank Accession No. (NID, PID, GI) | Reference |
| --- | --- | --- | --- | --- |
| sAtiepf | SEQ ID NO: 22 | 100 | BD171257 CDS-2, G 1: 27877069 | JP2001-006878, W002055715A1 |
| AGRL627 | SEQ ID NO: 24 | 88.7 | AGR_L_627, GI: 159186217 | |
| PaioII | SEQ ID NO: 30 | 41.3 | PANA_3268, GI: 291618821 | |
| BsioII | SEQ ID NO: 26 | 16.9 | BSU39680, G1: 16081019 | Yoshida et al. (AEM72, 2006) |
| CgioII0169 | SEQ ID NO: 28 | 10.1 | NCgl0169, GI: 19551422 | |

Exemplary Embodiment 4: Establishment of Optimal Culture Conditions for D-chiro-inositol-producing Strains Out of the recombinant plasmid prepared in the Exemplary Embodiment 3, pCOLAD-Cgiep-Paioll is introduced into *E. coli* BL21(DE3) strain along with pACYCD-StiolT1-StiolT2(F2), so that an attempt is made to optimize culture of the recombinant strain.

4-1. Survey of D-chiro-inositol Productivity According to Culture Temperatures

A 50 mL is cultured in a baffled conical flask of 300 mL for about 40 hours under the culture conditions of 30° C., 37° C. and 180 rpm by using a terrific broth (TB) containing 15% (w/v) myo-inositol, 50 mg/L of chloramphenicol and 50 mg/L of kanamycin. For induction, IPTG is added at a concentration of 1 mM at OD 0.6. Out of the culture conditions, a concentration of myo-inositol added is determined in accordance with solubility (approximately 16-17% (w/v) at a corresponding temperature.

Figure 6A:
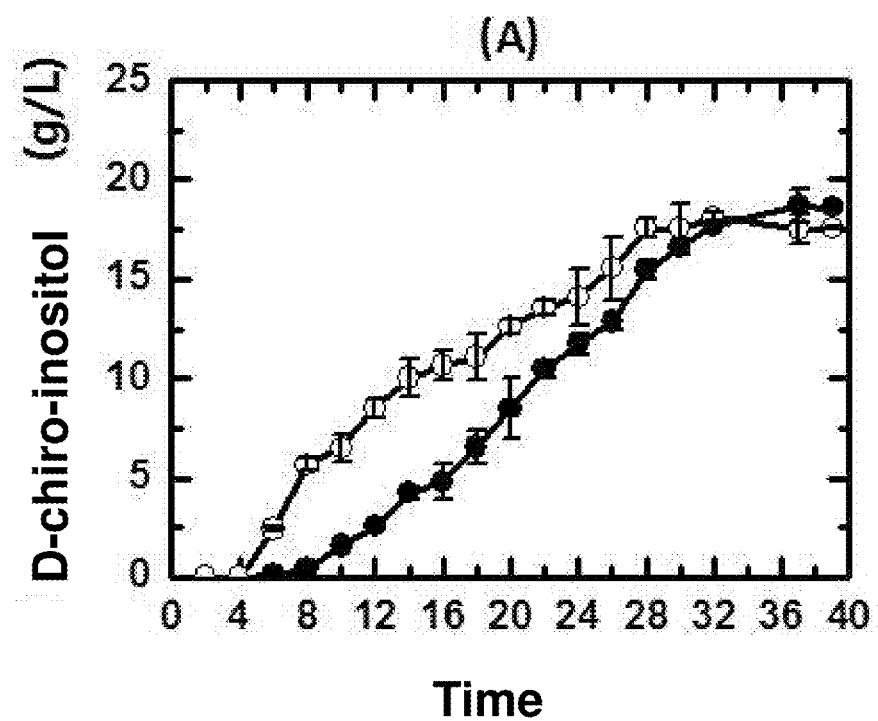
FIGS. 6a to 6c show a result of measuring a conversion ratio of D-chiro-inositol from myo-inositol in an inventive transformed *E. coli* according to culture temperatures. A test group for each symbol is as shown below; ●: 30° C. and o: 37 in FIG. 6a. o: microbe growth, ●: pH and ▲: amount of remaining glycerol at the temperature of 30° C.
Figure 6B:
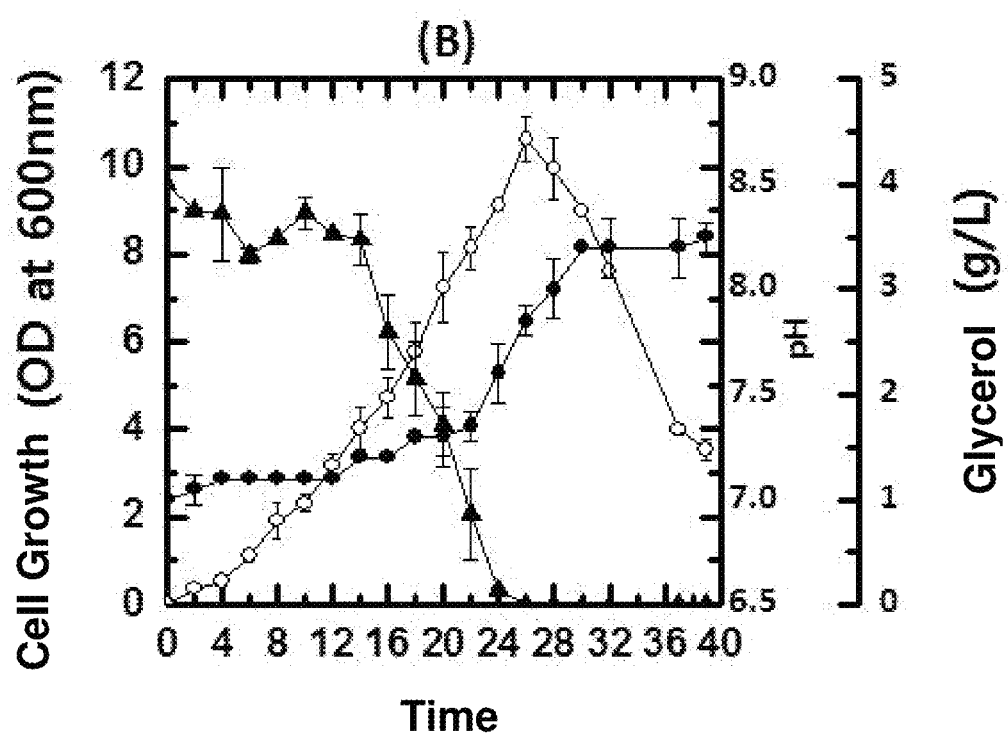
Figure 6C:
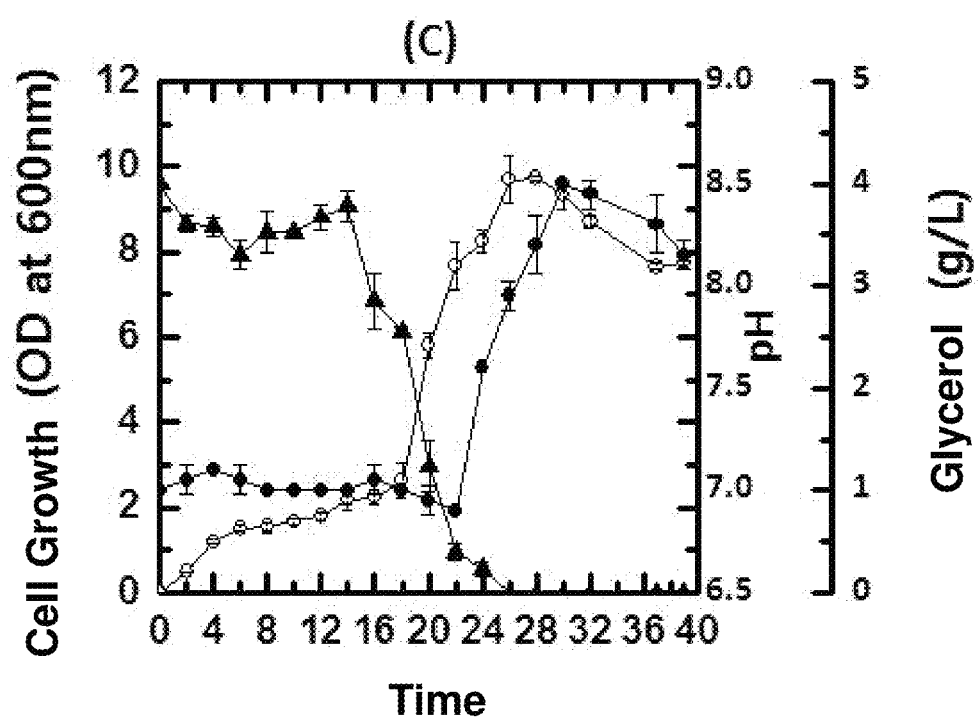

For the analysis of myo-inositol and D-chiro-inositol, a culture fluid is put into centrifugation, 1 mL of culture supernatant is taken out, boiled for 10 minutes, put into centrifugation again, and 500 uL of the resulting supernatant is taken out. The pre-treated culture supernatant is analyzed with HPLC (Shimadzu LC10Avp). When it comes to analysis conditions, Kromasil 5NH2 column (4.6 mm×250 mm), mobile phase 75% acetonitrile, column temperature 40° C. and an RI detector are used. The results thereof are shown in FIG. 6.

A carbon source glycerol out of a TB medium runs out in about 24 hours at both 30° C. and 37° C., and a microbe growth also comes to stop in about 24 hours accordingly. For 24 hours when the carbon source runs out and the microbe growth comes to stop, about 12 g/L of D-chiro-inositol is produced at 30° C. and about 14 g/L thereof is produced at 37° C., which is about 1.2 times higher than the former. Even after the microbe growth comes to stop, D-chiro-inositol is continuously converted so as to increase up to about 19 g/L at 37° C. in about 28 hours and at 30° C. in about 32 hours, respectively.

Such conversion from myo-inositol into D-chiro-inositol is known as involving reaction equilibrium (Yoshida et al., AEM72, 2006). In other words, physicochemical reaction equilibrium of about 86:14 is involved in between myo-inositol and D-chiro-inositol, so the amount of D-chiro-inositol corresponding to 150 g/L of myo-inositol is about 20 g/L. This is experimentally confirmed in this exemplary embodiment, too. In other words, in case of culturing with D-chiro-inositol added therein, myo-inositol is produced close to a reaction equilibrium ratio (results are not indicated). As a result, 19 g/L of D-chiro-inositol prepared amounts to the maximum of culture with 150 g/L of myo-inositol added therein. At 37° C., a time required for reaching such reaction equilibrium is about four hours faster than that of 30° C. In result, as far as a culture temperature is concerned, it is confirmed that 37° C. is an appropriate culture temperature.

4-2. Productivity of D-chiro-inositol According to Induction Time

Figure 7:
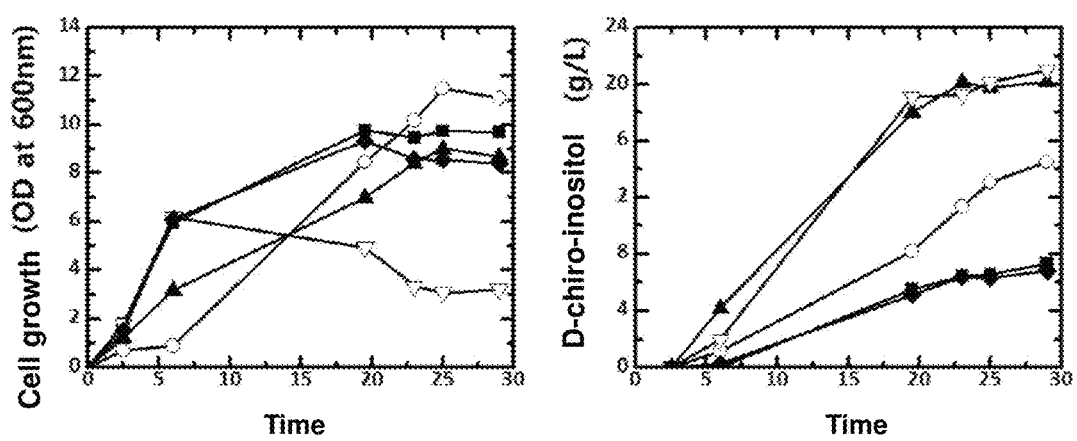
FIG. 7 shows a result of measuring a conversion ratio of D-chiro-inositol from myo-inositol according to induction time when culturing the transformed *E. coli* of the present invention. A test group for each symbol is as shown below; ■: no induction, o: induction at time 0, ▲: induction at OD 0.6, ▼: induction at OD 3 and ◆: induction at OD 10.

The productivity of D-chiro-inositol according to induction time of *E. coli* BL21 (DE3) strain, in which pACYCD-StiolT1-StiolT2(F2) and pCOLAD-Cgiep-Paioll are introduced, is considered. Assuming that a group without an inducer IPTG added is a negative control group, such productivity is checked at 37° C. while injecting at an initial time 0, OD 0.6, OD 3 and OD 10, respectively. Other culture conditions are as shown in 4-1 above, and the results of culture are shown in FIG. 7.

A very low productivity of D-chiro-inositol is shown in a group without IPTG-caused induction and a group in which IPTG is added to cause induction at OD 10 after growth comes to an end completely. In a group in which IPTG is injected upon the start of culture, it appears that a microbe growth is seriously hindered in the early stage of culture. When induction also occurs at OD 0.6 and OD 3, it seems that a microbe growth is immediately hindered. That's probably because a nitrogen source, a carbon source, etc., which should have been used for microbe growth, is actually consumed for protein synthesis while protein is expressed by means of IPTG, or probably because a membrane is damaged due to an inositol transporter protein. In result, it is confirmed that it is most preferable to inject an inducer when a microbe is adapted to a new medium environment at an early logarithmic phase and starts a logarithmic growth.

Figure 8:
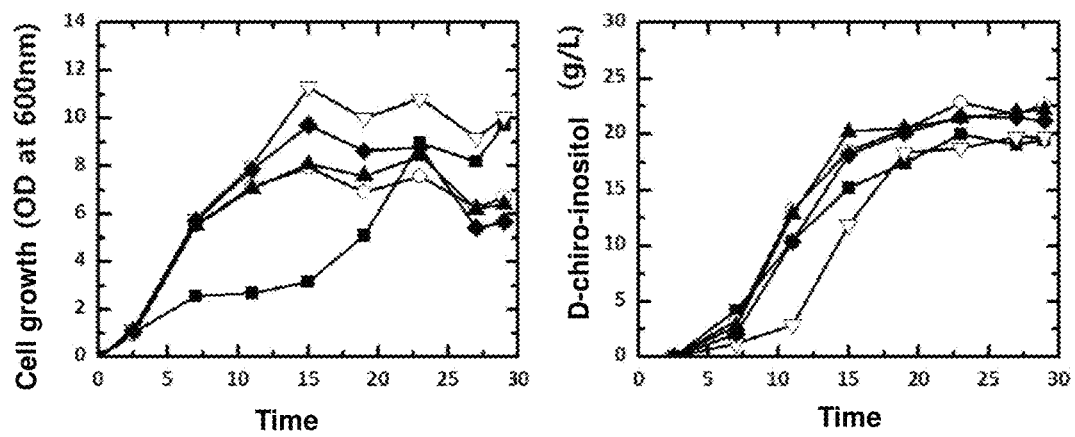
FIG. 8 shows a result of measuring a conversion ratio of D-chiro-inositol from myo-inositol according to induction types when culturing the transformed *E. coli* of the present invention. A test group for each symbol is as shown below; ■: add 1 mM IPTG at OD 0.6, o: add 0.5% lactose at time 0, ▲: add 0.5% lactose at OD 0.6, ▼: add 0.5% lactose at time OD 7, and ◆: add 0.1% lactose at time OD 0.6.

4-3. Confirmation of Productivity of D-chiro-inositol According to Inducer Types The productivity of D-chiro-inositol according to inducer types of *E. coli* BL21(DE3), in which pACYCD-StiolT1-StiolT2(F2) and pCOLAD-Cgiep-Paioll are introduced, is considered. As an inducer IPTG has a tendency to hinder cell growth, lactose, which can replace IPTG, is added as an inducer. Lactose is added by adjusting its time and amount of addition, and 0.5% (w/v) lactose is added at an early stage, OD 0.6 and OD 7, or 0.1% (w/v) lactose is added at OD 0.6. Other culture conditions are the same as shown in 4-1 above, and the results thereof are shown in FIG. 8. In case of IPTG, it is confirmed that an early growth is hindered as shown in the results of 4-2 above, but such hindrance is not found in a group with lactose added. When 0.5% lactose is added at an early stage, a production speed of D-chiro-inositol is fastest. When 0.5% lactose is added at OD 7, it is confirmed that D-chiro-inositol starts to produce late accordingly. Lactose is formed into allolactose by lacZ gene, which is expressed while a microbe grows, thus activating a T7 promoter of the inventive expression vector. In other words, only when a microbe starts to grow, adapting itself to myo-inositol of high concentration, that is, a high osmotic pressure environment, the promoter is activated. So, such expression by lactose seems to reduce toxicity to the microbe.

According to the Exemplary Embodiment 4 above, the optimal culture condition is determined in such a way that lactose is added to a culture medium in advance by using a TB medium and cultured at 37° C. And such condition is used to perform a subsequent experiment.

Figure 9:
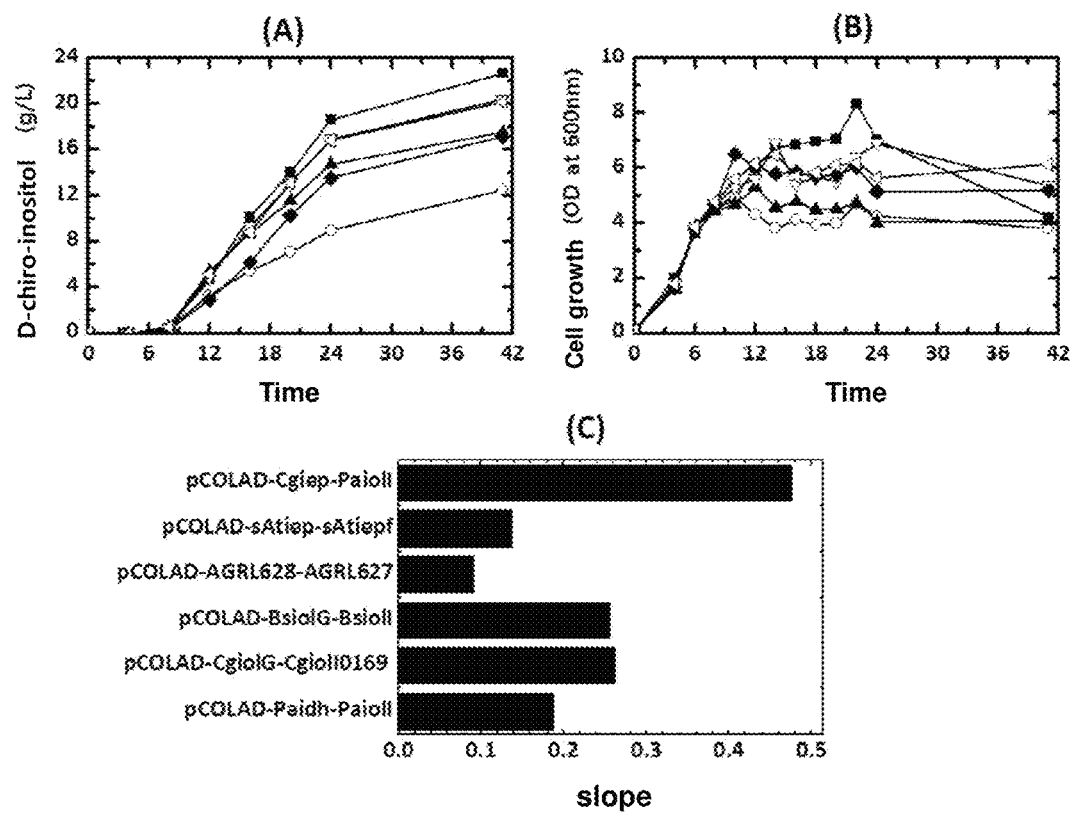
FIG. 9 shows a result of measuring a D-chiro-inositol production rate (panel A), a microbe growth (panel B) and a gradient of production speed (panel C), with regard to a recombinant strain obtained by introducing the inositol dehydrogenase and inosose isomerase genes derived from various strains and a combination thereof. An experiment was performed by introducing an inositol transporter expression recombinant plasmid vector pACYCD-StiolT1-StiolT2 together to a transformed *E. coli*. A test group for each symbol is as shown below; ■: pCOLAD-Cgiep-PaiolI, o: pCOLAD-sAtiep-sAtiepf, ▲: pCOLAD-AGRL628-AGRL627, ▼: pCOLAD-BsiolG-Bsioill, ◆: pCOLAD-Cgi-olG-CgiolIC>169 and >: pCOLAD-Paidh-PaiolI.

Exemplary Embodiment 5: Comparison of Activity Between D-chiro-inositol Converting Genes Each of pCOLAD-sAtiep-sAtiepf, pCOLAD-AGRL628-AGRL627, pCOLAD-BsiolG-Bsioll, pCOLAD-CgiolG-Cgioll0169, pCOLAD-Paidh-Paioll and pCOLAD-Cgiep-Paioll, which are expression vectors for expressing the inositol dehydrogenase and inosose isomerase constructed in the Exemplary Embodiment 3, is introduced into *E. coli* BL21 (DE3) along with a pACYCD-StiolT1-StiolT2, an inositol transporter, whose transporter activity is confirmed in the Exemplary Embodiment 2, so that six kinds of recombinant strains are prepared. The recombinant strains prepared above are cultured by using the optimal fermentation conditions tested in the Exemplary Embodiment 4. The results of measuring culture are shown in FIG. 9.

In terms of a production speed (panel C of FIG. 9) of logarithmic production time (about 8 to 24 hours) of D-chiro-inositol, a recombinant plasmid pCOLAD-AGRL628-AGRL627 shows the lowest production speed at 0.09, while pCOLAD-sAtiep-sAtiepf (WO 02/055715) also shows the lowest production at 0.14. In a gene selected in the present invention, it appears that myo-inositol dehydrogenase and inosose isomerase are converted into D-chiro-inositol at the fastest speed of a gradient 0.48 in combination with Cgiep and Paioll, respectively, that is, pCOLAD-Cgiep-Paioll. Such gradient value is about 5.3 times faster than the lowest speed of pCOLAD-AGRL628-AGRL627 and 1.8 times higher than the second speed of pCOLAD-CgiolG-Cgioll0169 (0.26). The concentration of D-chiro-inositol produced after a 40-hour culture is highest in the case of pCOLAD-Cgiep-Paioll. A final microbe growth speed comes to a pause phase before about 12 hours as a whole, and a microbe concentration is also lowest in pCOLAD-sAtiep-sAtiepf in proportionate to a production speed of D-chiro-inositol above. In result, when pCOLAD-Cgiep-Paioll is introduced, 22.7 g/L of D-chiro-inositol is converted from 150 g/L of myo-inositol and a conversion rations is about 15.1%. In case of pCOLAD-sAtiep-sAtiepf showing the lowest conversion ratio, about 12.5 g/L thereof is converted and a conversion ratio remains at about 8.3%. A fermentation experiment is performed in such a way that a recombinant *E. coli* strain, in which pCOLAD-Cgiep-Paioll is introduced from the results, is a producing strain.

Figure 10:
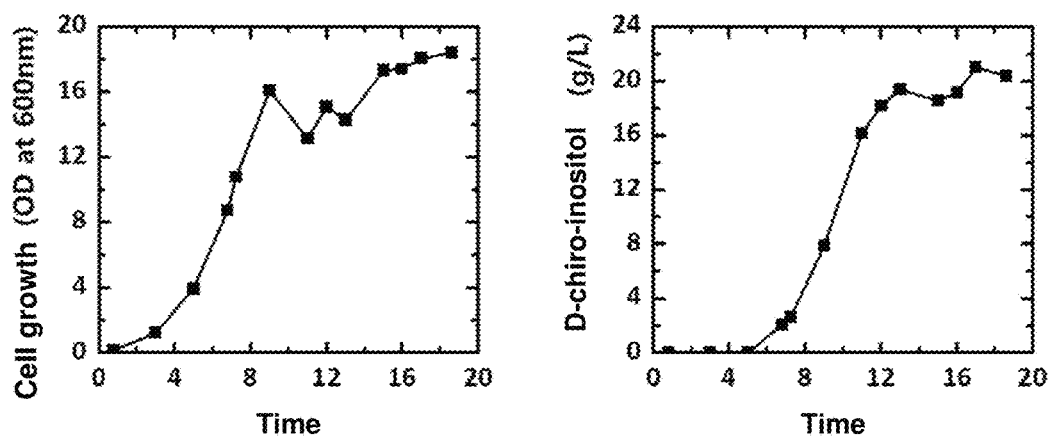
FIG. 10 shows a result of checking the preparation of D-chiro-inositol from myo-inositol by performing 1 L fermentation under optimal conditions by using the transformed *E. coli* which is selected in the present invention.

Exemplary Embodiment 6: Increase in Production Through Fermentation of Recombinant Strains 1 L fermentation is performed by using the optimal recombinant strain obtained from the results of optimizing culture and selecting excellent genes performed above. Fermentation is performed in a 1 L capacity in a 3 L fermentation tank of MARADO-PDA [CNS Co., Ltd. Daejeon, Korea]. A 2YT medium is used for seed culture. In this culture, 15% myo-inositol and 0.5% lactose are added to a TB medium. A 50 mL of seed culture fluid, which was cultured up to OD 3, is inoculated into the fermentation tank, which was stabilized with a temperature, pH and OD, and then cultured for about 20 hours. A fermentation temperature is adjusted to 37° C. and pH is adjusted to 7.0 by using ammonia water. After OD is reduced to 40% or less, RPM is increased to maintain 40% or more. The results of fermentation are shown in FIG. 10. A microbe reaches up to about OD 18 within 18 hours. D-chiro-inositol reaches about 20 g/L, which is an equilibrium concentration within about 12 hours, and after then it is not increased any more.

Exemplary Embodiment 7: Fractionation and GC-MS Analysis of D-chiro-inositol Prepared Fraction of D-chiro-inositol prepared from microbes is performed by using HPLC (Shimadzu LCIOAvp). When it comes to analysis conditions, Kromasil 5NH2 Prep Column (10 mm×250 mm), mobile phase 75% acetonitrile, column temperature 40° C. and an RI detector are used. A 1004 of test sample is injected and flowed at a flow speed of 4 mL/min, so that an effluent for a corresponding peak is taken out. The effluent collected is concentrated and dried by using a vacuum condenser (EYELA, Japan), dissolved in 5 mL of distilled water, and GC-MS analysis is performed.

Figure 11:
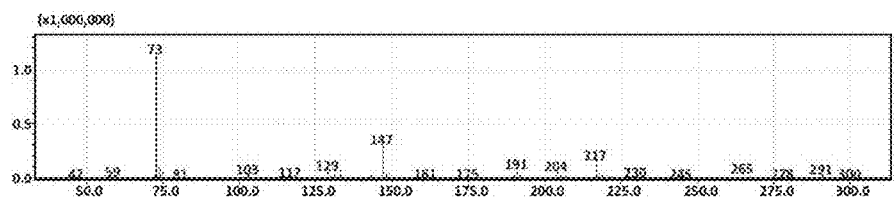
FIG. 11 shows a result of performing GC-MS analysis on a D-chiro-inositol fraction prepared by a stain of the present invention.
Figure 11:
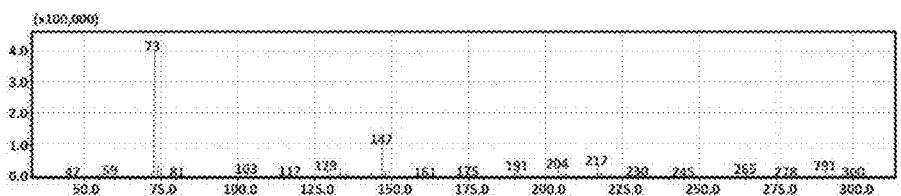

GC-MS analysis is performed by using Shimadzu GCMS-QP2010. For treatment before analysis, 1 mg of sample is dissolved in a 1 mg of 1-trimethylsylyl-imidazole and pyridine mixed at a ratio of 1:1 and is reacted at 70° C. for 30 minutes so as to be used for analysis. For analysis conditions, HP-1 capillary column (30 m Length, 0.25 mm ID, 0.25 μm Film) is used and 1 μL of sample is injected into a split mode injector (1:50) and analyzed at a flow rate of 1 mL/min. A sample injection temperature is 280° C., an oven temperature is maintained at 150° C. for two minutes, increased up to 300° C. at a speed of 20° C./min, and maintained for two minutes. An MS profile for analysis results is compared with a profile of standard sample D-chiro-inositol (Sigma 468045, U.S.A.) and the results thereof are shown in FIG. 11. As a result, it is confirmed that the MS profile is accurately the same as the profile of standard sample.

As the specific parts of the present invention have been described in detail above, such detailed description of the disclosed invention are only preferred examples of the present invention to the person with ordinary skill in the art, and it is clear that they are not used to limit the range of the present invention disclosed in the claims. Therefore, the actual range of the present invention is defined by the following claims and equivalents thereof.

This application contains references to amino acid sequences and/or nucleic acid sequences which have been submitted herewith as the sequence listing text file. The aforementioned sequence listing is hereby incorporated by reference in its entirety pursuant to 37 C.F.R. §1.52(e).

What is claimed is:

1. A method for preparing D-chiro-inositol from myo-inositol, comprising:
   (a) transforming a host cell with (i) a recombinant vector comprising a myo-inositol transporter coding DNA sequence operatively linked to a promoter; and (ii) a recombinant vector comprising an inositol dehydrogenase coding DNA sequence and an inosose isomerase coding DNA sequence operatively linked to a promoter; and
   (b) culturing the host cell of (a) in a medium comprising myo-inositol, thereby preparing D-chiro-inositol,
   wherein the host cell is selected from the group consisting of a mammalian cell, an insect cell, a yeast cell, and a prokaryotic cell,
   wherein the myo-inositol transporter has the amino acid sequence set forth in SEQ ID NO: 3,
   wherein the inositol dehydrogenase has the amino acid sequence set forth in SEQ ID NO: 31, and
   wherein the inosose isomerase has the amino acid sequence set forth in SEQ ID NO: 30.

2. The method of claim 1, wherein the host cell is a prokaryotic cell.

3. The method of claim 1, further comprising (c) separating D-chiro-inositol from a culture product of the transformed host cell after the step (b).

4. A host cell, transformed with a recombinant vector, the recombinant vector comprising: (i) a myo-inositol transporter coding DNA sequence operatively linked to a promoter; and (ii) an inositol dehydrogenase coding DNA sequence and an inosose isomerase coding DNA sequence which are operatively linked to a promoter,
   wherein the host cell is selected from the group consisting of a mammalian cell, an insect cell, a yeast cell, and a prokaryotic cell,
   wherein the myo-inositol transporter has the amino acid sequence set forth in SEQ ID NO: 3,
   wherein the inositol dehydrogenase has the amino acid sequence set forth in SEQ ID NO: 31, and
   wherein the inosose isomerase has the amino acid sequence set forth in SEQ ID NO: 30.

5. A composition for preparing D-chiro-inositol from myo-inositol comprising the host cell of claim 4.

6. A recombinant vector kit for preparing D-chiro-inositol from myo-inositol, comprising: (i) a recombinant vector comprising a myo-inositol transporter DNA coding sequence operatively linked to a promoter; and (ii) a recombinant vector comprising an inositol dehydrogenase coding DNA sequence and an inosose isomerase coding DNA sequence operatively linked to a promoter as an active component,
   wherein the myo-inositol transporter has the amino acid sequence set forth in SEQ ID NO: 3,
   wherein the inositol dehydrogenase has the amino acid sequence set forth in SEQ ID NO: 31, and
   wherein the inosose isomerase has the amino acid sequence set forth in SEQ ID NO: 30.

* * * * *

SEQUENCE LISTING

```
<160> NUMBER OF SEQ ID NOS: 51

<210> SEQ ID NO 1
<211> LENGTH: 473
<212> TYPE: PRT
<213> ORGANISM: Bacillus subtilis

<400> SEQUENCE: 1

Met Asn Lys Gln Gly Asn Gln Met Ser Phe Leu Arg Thr Ile Ile Leu
1               5                   10                  15

Val Ser Thr Phe Gly Gly Leu Leu Phe Gly Tyr Asp Thr Gly Val Leu
            20                  25                  30

Asn Gly Ala Leu Pro Tyr Met Gly Glu Pro Asp Gln Leu Asn Leu Asn
        35                  40                  45

Ala Phe Thr Glu Gly Leu Val Thr Ser Ser Leu Leu Phe Gly Ala Ala
    50                  55                  60
```

```
Leu Gly Ala Val Phe Gly Gly Arg Met Ser Asp Phe Asn Gly Arg Arg
 65                  70                  75                  80

Lys Asn Ile Leu Phe Leu Ala Val Ile Phe Ile Ser Thr Ile Gly
                 85                  90                  95

Cys Thr Phe Ala Pro Asn Val Thr Val Met Ile Ile Ser Arg Phe Val
                100                 105                 110

Leu Gly Ile Ala Val Gly Gly Ala Ser Val Thr Val Pro Ala Tyr Leu
                115                 120                 125

Ala Glu Met Ser Pro Val Glu Ser Arg Gly Arg Met Val Thr Gln Asn
            130                 135                 140

Glu Leu Met Ile Val Ser Gly Gln Leu Leu Ala Phe Val Phe Asn Ala
145                 150                 155                 160

Ile Leu Gly Thr Thr Met Gly Asp Asn Ser His Val Trp Arg Phe Met
                165                 170                 175

Leu Val Ile Ala Ser Leu Pro Ala Leu Phe Leu Phe Phe Gly Met Ile
                180                 185                 190

Arg Met Pro Glu Ser Pro Arg Trp Leu Val Ser Lys Gly Arg Lys Glu
            195                 200                 205

Asp Ala Leu Arg Val Leu Lys Lys Ile Arg Asp Glu Lys Arg Ala Ala
210                 215                 220

Ala Glu Leu Gln Glu Ile Glu Phe Ala Phe Lys Lys Glu Asp Gln Leu
225                 230                 235                 240

Glu Lys Ala Thr Phe Lys Asp Leu Ser Val Pro Trp Val Arg Ile
                245                 250                 255

Val Phe Ile Gly Leu Gly Ile Ala Ile Val Gln Gln Ile Thr Gly Val
                260                 265                 270

Asn Ser Ile Met Tyr Tyr Gly Thr Glu Ile Leu Arg Asn Ser Gly Phe
                275                 280                 285

Gln Thr Glu Ala Ala Leu Ile Gly Asn Ile Ala Asn Gly Val Ile Ser
            290                 295                 300

Val Leu Ala Thr Phe Val Gly Ile Trp Leu Leu Gly Arg Val Gly Arg
305                 310                 315                 320

Arg Pro Met Leu Met Thr Gly Leu Ile Gly Thr Thr Ala Leu Leu
                325                 330                 335

Leu Ile Gly Ile Phe Ser Leu Val Leu Glu Gly Ser Pro Ala Leu Pro
                340                 345                 350

Tyr Val Val Leu Ser Leu Thr Val Thr Phe Leu Ala Phe Gln Gln Gly
            355                 360                 365

Ala Ile Ser Pro Val Thr Trp Leu Met Leu Ser Glu Ile Phe Pro Leu
            370                 375                 380

Arg Leu Arg Gly Leu Gly Met Gly Val Thr Val Phe Cys Leu Trp Met
385                 390                 395                 400

Val Asn Phe Ala Val Ser Phe Thr Phe Pro Ile Leu Leu Ala Ala Ile
                405                 410                 415

Gly Leu Ser Thr Thr Phe Phe Ile Phe Val Gly Leu Gly Ile Cys Ser
                420                 425                 430

Val Leu Phe Val Lys Arg Phe Leu Pro Glu Thr Lys Gly Leu Ser Leu
                435                 440                 445

Glu Gln Leu Glu Glu Asn Phe Arg Ala Tyr Asp His Ser Gly Ala Lys
            450                 455                 460

Lys Asp Ser Gly Ala Glu Val Ile Gly
465                 470
```

```
<210> SEQ ID NO 2
<211> LENGTH: 438
<212> TYPE: PRT
<213> ORGANISM: Bacillus subtilis

<400> SEQUENCE: 2

Met Gly Asn Thr Asn Gly Asp Ser Ala Phe Asn Lys Arg Thr Ile Ala
1               5                   10                  15

Ala Ala Leu Ala Asn Tyr Ile Asp Ala Gly Ser Ile Val Ala Gly Ser
            20                  25                  30

Ala Gly Leu Ser Leu Trp Val Ser Tyr Leu Lys Leu Ser Asp Thr Gln
        35                  40                  45

Ile Gly Leu Leu Gly Ala Leu Ser Ala Asn Ala Ile Ser Ala Ala Val
    50                  55                  60

Gly Ala Leu Leu Gly Gly Phe Leu Ala Asp Lys Val Gly Arg Lys Ala
65                  70                  75                  80

Val Tyr Thr Asn Ser Met Leu Val Tyr Ala Leu Gly Ile Cys Leu Val
                85                  90                  95

Leu Phe Gly Val Asn Phe Pro Met Leu Leu Ser Gly Tyr Ile Ile Ile
            100                 105                 110

Gly Leu Ser Val Gly Ala Asp Ile Thr Ala Ser Trp Thr Ile Ile Ala
        115                 120                 125

Glu Asn Ala Pro Lys Lys Asn Arg Ala Arg His Cys Gly Val Ala Gln
    130                 135                 140

Val Ala Trp Ala Ala Gly Ala Val Val Leu Leu Leu Ser Val Leu
145                 150                 155                 160

Ala Gly Asp Leu Gly Leu Leu Gly Asn Lys Ile Val Phe Ala His Leu
                165                 170                 175

Leu Val Ile Ala Leu Ile Thr Tyr Ile Leu Arg Ile Arg Leu Pro Glu
            180                 185                 190

Ser Asp Ala Trp Gln Thr Lys Asn Gln Pro Glu Glu Ala Gln Ala Glu
        195                 200                 205

Lys Pro Ala Val Leu Asn Lys Thr Ser Tyr Phe Asp Leu Leu Lys Pro
    210                 215                 220

Met Tyr Leu Lys Ser Ile Leu Phe Leu Met Gly Val Tyr Leu Val Trp
225                 230                 235                 240

Asn Leu Ala Ala Gly Val Met Gly Phe Phe Met Pro Tyr Ile Tyr Gln
                245                 250                 255

Gln Val Gly Gly Val Ser Ala Asn Met Ala Asn Leu Leu Gln Met Gly
            260                 265                 270

Leu Phe Ile Phe Thr Gly Leu Gly Val Ala Leu Ile Phe Met Pro Phe
        275                 280                 285

Ala Asp Lys Tyr Arg Lys Thr Val Phe Gly Ile Ala Ala Phe Met Ala
    290                 295                 300

Val Ile Gly Trp Thr Leu Phe Leu Leu Pro Val Glu Gly Leu Pro Ile
305                 310                 315                 320

Leu Leu Leu Phe Ile Val Val Ile Gly Ile Asn Asn Gly Ala Gly Gln
                325                 330                 335

Gln Ala Asn Tyr Gln Leu Trp Ala Ser Glu Ile Phe Pro Thr Gln Tyr
            340                 345                 350

Arg Ala Ser Ala Gln Gly Leu Met Phe Phe Leu Val Arg Ile Ser Ile
        355                 360                 365

Gly Ile Trp Ser Leu Phe Val Pro Met Ile Ile Thr Asn Phe Gly Ile
    370                 375                 380
```

```
Gly Thr Met Ala Ala Ile Leu Leu Gly Cys Val Thr Ala Ser Met Ile
385                 390                 395                 400

Ile Gly Leu Leu Phe Ala Pro Asn Thr Ser Gly Lys Ser Leu Glu Gln
                405                 410                 415

Ile Gln Glu Glu Leu Tyr Gly Ser Pro Gln Ser Gln Val Lys Lys Gly
            420                 425                 430

Thr Glu Ser Lys Ile Met
            435

<210> SEQ ID NO 3
<211> LENGTH: 477
<212> TYPE: PRT
<213> ORGANISM: Salmonella typhimurium

<400> SEQUENCE: 3

Met Ser Thr Ser Asp Ser Cys Tyr Asn Thr Gly Tyr Ile Leu Arg Ile
1               5                   10                  15

Cys Ala Ile Ala Ala Leu Gly Gly Ile Leu Phe Gly Tyr Asp Thr Ala
                20                  25                  30

Val Ile Ser Gly Ala Ile Gly Ser Leu Thr Ser Tyr Phe His Leu Ser
            35                  40                  45

Pro Ala Glu Thr Gly Trp Ala Val Ser Cys Val Val Gly Cys Val
    50                  55                  60

Ile Gly Ser Phe Ser Ala Gly Tyr Leu Ser Lys Arg Phe Gly Arg Lys
65                  70                  75                  80

Lys Ser Leu Met Val Ser Ala Leu Leu Phe Thr Ile Ser Ala Val Gly
                85                  90                  95

Thr Ser Leu Ser Tyr Thr Phe Thr His Phe Val Ile Tyr Arg Ile Ile
                100                 105                 110

Gly Gly Leu Ala Val Gly Leu Ala Ala Thr Val Ser Pro Met Tyr Met
            115                 120                 125

Ser Glu Val Ser Pro Lys Asn Met Arg Gly Arg Ala Leu Ser Met Gln
    130                 135                 140

Gln Phe Ala Ile Val Phe Gly Gln Ile Leu Ile Phe Tyr Val Asn Tyr
145                 150                 155                 160

Lys Ile Ala Ser Ile Ala Ala Asp Thr Trp Leu Ile Glu Leu Gly Trp
                165                 170                 175

Arg Tyr Met Phe Ala Ala Gly Ile Ile Pro Cys Ile Leu Phe Cys Ile
            180                 185                 190

Leu Val Phe Leu Ile Pro Glu Ser Pro Arg Trp Met Met Ile Gly
    195                 200                 205

Arg Glu Glu Glu Thr Leu Lys Ile Leu Thr Lys Ile Ser Asn Glu Glu
210                 215                 220

His Ala Arg His Leu Leu Ala Asp Ile Lys Thr Ser Leu Gln Asn Asp
225                 230                 235                 240

Gln Leu Asn Ala His Gln Lys Leu Asn Tyr Arg Asp Gly Asn Val Arg
                245                 250                 255

Phe Ile Leu Ile Leu Gly Cys Met Ile Ala Met Leu Gln Gln Val Thr
            260                 265                 270

Gly Val Asn Val Met Met Tyr Tyr Ala Pro Ile Val Leu Lys Asp Val
        275                 280                 285

Thr Gly Ser Ala Gln Glu Ala Leu Phe Gln Thr Ile Trp Ile Gly Val
    290                 295                 300

Ile Gln Leu Ile Gly Ser Ile Ile Gly Ala Met Ile Met Asp Lys Met
```

```
            305                 310                 315                 320
Gly Arg Leu Ser Leu Met Arg Lys Gly Thr Ile Gly Ser Ile Ile Gly
                    325                 330                 335

Leu Leu Leu Thr Ser Trp Ala Leu Tyr Ser Gln Ala Thr Gly Tyr Phe
                340                 345                 350

Ala Leu Phe Gly Met Leu Phe Phe Met Ile Phe Tyr Ala Leu Ser Trp
            355                 360                 365

Gly Val Gly Ala Trp Val Leu Ile Ser Glu Ile Phe Pro Asn Arg Met
        370                 375                 380

Arg Ser Gln Gly Met Ser Ile Ser Val Gly Phe Met Trp Met Ala Asn
385                 390                 395                 400

Phe Leu Val Ser Gln Phe Pro Met Ile Asn Glu Asn Pro Tyr Leu
                405                 410                 415

Leu Ser His Phe His Gly Ala Phe Pro Met Trp Ile Phe Ala Ile Cys
                420                 425                 430

Cys Ile Phe Ser Tyr Phe Phe Ile Cys Arg Tyr Leu Pro Glu Thr Lys
                435                 440                 445

Gly Ile Ser Leu Glu Lys Met Glu Ser Val Val Leu Ala Lys Arg Arg
        450                 455                 460

Lys Lys Leu Gln Pro Ile Gln Thr Glu Arg Tyr Ser Asp
465                 470                 475

<210> SEQ ID NO 4
<211> LENGTH: 478
<212> TYPE: PRT
<213> ORGANISM: Salmonella typhimurium

<400> SEQUENCE: 4

Met Ser Gln Arg Ser Lys Tyr Asn Ser Ala Tyr Val Tyr Val Leu Cys
1               5                   10                  15

Cys Ile Ala Ala Leu Ala Gly Leu Met Phe Gly Tyr Ser Thr Ala Val
                20                  25                  30

Ile Thr Gly Val Val Leu Pro Leu Gln Gln Tyr Tyr Gln Leu Thr Pro
            35                  40                  45

Thr Glu Thr Gly Trp Ala Val Ser Ser Ile Val Ile Gly Cys Ile Ile
        50                  55                  60

Gly Ala Leu Val Gly Gly Lys Ile Ala Asp Lys Leu Gly Arg Lys Pro
65                  70                  75                  80

Ala Leu Leu Ile Ile Ala Ile Ile Phe Ile Ala Ser Ser Leu Gly Ala
                85                  90                  95

Ala Met Ser Glu Ser Phe Met Ile Phe Ser Leu Ser Arg Ile Val Cys
                100                 105                 110

Gly Phe Ala Val Gly Met Ala Gly Thr Ala Ser Thr Met Tyr Met Ser
            115                 120                 125

Glu Leu Ala Pro Ala Glu Ile Arg Gly Lys Ala Leu Gly Ile Tyr Asn
        130                 135                 140

Ile Ser Val Val Ser Gly Gln Val Ile Val Phe Ile Val Asn Tyr Leu
145                 150                 155                 160

Ile Ala Lys Gly Met Pro Ala Asp Val Leu Val Ser Gln Gly Trp Lys
                165                 170                 175

Thr Met Leu Phe Ala Gln Val Val Pro Ser Ile Ala Met Leu Ala Ile
                180                 185                 190

Thr Leu Phe Leu Pro Glu Ser Pro Ala Trp Cys Ala Arg Asn Asn Arg
            195                 200                 205
```

```
Ser Glu Ala Arg Ser Ile Lys Val Leu Thr Arg Ile Tyr Ser Gly Leu
    210                 215                 220

Thr Ala Thr Asp Val Ala Ala Ile Phe Asp Ser Met Lys Glu Thr Val
225                 230                 235                 240

Arg Ser Gln Asp Asn Val Ala Gly Gly Glu Arg Thr Asn Leu Lys Ser
                245                 250                 255

Ser Pro Val Leu Arg Tyr Ile Leu Leu Val Gly Cys Cys Ile Ala Val
            260                 265                 270

Leu Gln Gln Phe Thr Gly Val Asn Val Met Asn Tyr Tyr Ala Pro Leu
        275                 280                 285

Val Leu Gln Asn Ser Ser Thr Glu Val Val Met Phe Gln Thr Ile Phe
290                 295                 300

Ile Ala Val Cys Asn Val Val Gly Ser Phe Ile Gly Met Ile Leu Phe
305                 310                 315                 320

Asp Arg Tyr Gly Arg Ile Pro Ile Met Lys Ile Gly Thr Ile Gly Ser
                325                 330                 335

Ile Val Gly Leu Leu Ile Ala Ser Tyr Gly Leu Tyr Thr His Asp Thr
            340                 345                 350

Gly Tyr Ile Thr Ile Phe Gly Ile Leu Phe Phe Met Leu Leu Phe Ala
        355                 360                 365

Val Ser Trp Ser Val Gly Ala Trp Val Leu Ile Ser Glu Val Phe Pro
370                 375                 380

Glu Lys Ile Lys Gly Phe Gly Met Gly Leu Ala Val Ser Leu Met Trp
385                 390                 395                 400

Ile Ala Asn Phe Leu Ile Ser Leu Leu Phe Pro Val Ile Asn Asp Asn
                405                 410                 415

Ala Trp Leu Gln Glu Thr Phe Gly Gly Ala Phe Ser Met Trp Ile Phe
            420                 425                 430

Val Val Phe Asn Leu Val Cys Tyr Val Phe Ile Ser Arg Tyr Val Pro
        435                 440                 445

Glu Thr Lys Gly Val Pro Leu Thr Glu Ile Glu Arg Leu Ala Glu Asn
    450                 455                 460

Lys Leu Arg Glu Ile Gln Gly Lys Arg Arg Asp Val Ile Ala
465                 470                 475

<210> SEQ ID NO 5
<211> LENGTH: 461
<212> TYPE: PRT
<213> ORGANISM: Agrobacterium tumefaciens

<400> SEQUENCE: 5

Met Asn Ile Met Gln Pro Leu Arg Ala Asp Ala Thr Ala Val Ala Asp
1               5                   10                  15

Pro Gln Ala Asp Ile Ser Ala Arg Leu Glu Arg Leu Pro Ile Thr Arg
            20                  25                  30

Glu Val Phe Trp Ala Arg Asn Ile Val Gly Ala Ala Thr Phe Phe Asp
        35                  40                  45

Gly Tyr Thr Val Ile Ala Ile Ala Tyr Ala Met Pro Val Leu Val Arg
    50                  55                  60

Glu Trp Gly Leu Thr Pro Ser Gly Thr Gly Met Ile Leu Ser Met Gly
65                  70                  75                  80

Tyr Leu Gly Gln Leu Ile Gly Ala Ile Leu Phe Gly Trp Leu Ala Glu
                85                  90                  95

Arg Ile Gly Arg Leu Lys Val Leu Leu Phe Thr Ile Leu Leu Phe Val
            100                 105                 110
```

Ser Met Asp Val Ala Cys Leu Phe Ala Ala Gly Ala Gly Met Met Met
            115                 120                 125

Ala Phe Arg Phe Val Gln Gly Ile Gly Thr Gly Gly Glu Val Pro Val
    130                 135                 140

Ala Ser Ala Tyr Ile Asn Glu Leu Ile Gly Ser Lys Gly Arg Gly Arg
145                 150                 155                 160

Phe Phe Leu Leu Tyr Glu Val Met Phe Leu Leu Gly Leu Val Gly Ala
                165                 170                 175

Gly Leu Ile Gly Tyr Phe Met Val Pro Leu Tyr Gly Trp Lys Ala Met
            180                 185                 190

Phe Ile Val Gly Leu Val Pro Ala Met Leu Met Ile Pro Leu Arg Trp
            195                 200                 205

Phe Leu Lys Glu Ser Pro Arg Trp Leu Ala Ala Thr Gly Arg Tyr Asp
            210                 215                 220

Glu Ala Asn Val Ile Val Lys Arg Met Glu Glu Ser Ala Arg Ala Ala
225                 230                 235                 240

Gly Lys Ala Leu Pro Glu Pro Arg Ile Ile Ala Thr Pro Ala Lys Arg
                245                 250                 255

Val Ser Asp Trp Arg Glu Leu Phe Gln Gly Ile Tyr Leu Lys Arg Thr
            260                 265                 270

Leu Ser Ile Trp Ala Met Trp Phe Cys Ala Tyr Met Val Ala Asn Gly
            275                 280                 285

Thr Ile Thr Trp Leu Pro Thr Leu Tyr Arg Gln Thr Phe Asn Leu Pro
            290                 295                 300

Leu Glu Thr Ser Ile Leu Tyr Gly Phe Met Thr Ser Ala Ala Gly Val
305                 310                 315                 320

Val Ala Ala Val Ile Cys Ala Leu Leu Ile Asp Lys Val Gly Arg Lys
                325                 330                 335

Arg Trp Tyr Ala Gly Ala Leu Leu Ala Pro Val Pro Leu Ala Ile
            340                 345                 350

Leu Ala Trp Leu Gly Ala Thr Ser Pro Met Gln Val Leu Ile Phe Ala
            355                 360                 365

Gly Leu Ala Tyr Ala Ile Val Gln Thr Val Thr Phe Ser Leu Tyr Leu
            370                 375                 380

Tyr Ser Ala Glu Ile Tyr Pro Thr Arg Met Arg Ala Ile Gly Thr Gly
385                 390                 395                 400

Ala Gly Ser Ala Trp Leu Arg Leu Gly Ser Ser Ala Gly Pro Met Leu
                405                 410                 415

Val Gly Phe Val Met Ser Ser Met Gly Ile Gln Tyr Val Phe Ala Thr
            420                 425                 430

Phe Ala Phe Ile Leu Ile Ile Gly Ala Val Val Thr Met Leu Phe Ala
            435                 440                 445

Val Glu Thr Lys Gly Lys Val Leu Glu Glu Leu Ser Pro
450                 455                 460

<210> SEQ ID NO 6
<211> LENGTH: 449
<212> TYPE: PRT
<213> ORGANISM: Agrobacterium tumefaciens

<400> SEQUENCE: 6

Met Gln Gly Arg Gly Asp Ala Asp Pro Tyr Arg Met Ala Arg Ser Cys
1               5                   10                  15

Val Lys Gly Arg Asn Met Ser Thr Asn Tyr Leu Ser Ala Ala Ser Val

```
                 20                  25                  30
Arg Thr Lys Asn Pro Ala Gly Val Ile Ala Thr Cys Gly Leu Met Ile
                 35                  40                  45
Met Phe Asp Gly Tyr Asp Leu Val Val Tyr Gly Ala Val Pro Ala
 50                  55                  60
Leu Leu Lys Glu Ser Thr Trp Ala Leu Asn Pro Ala Met Val Gly Arg
 65                  70                  75                  80
Ala Ala Ala Leu Thr Leu Val Gly Met Leu Gly Ala Leu Phe Ala
                 85                  90                  95
Gly Thr Met Ala Asp Arg Ile Gly Arg Arg Lys Val Val Leu Leu Ser
                100                 105                 110
Leu Ala Gly Phe Ser Ala Met Met Ile Ala Ser Ala Met Thr Pro Asn
                115                 120                 125
Phe Leu Ala Phe Glu Ile Thr Arg Phe Ala Gly Leu Gly Leu Gly
                130                 135                 140
Ala Leu Leu Pro Thr Val Thr Ala Leu Val Leu Glu Phe Ser Pro Pro
145                 150                 155                 160
Gln Arg Arg Ala Gln Ala Asn Ser Leu Ser Phe Leu Gly Tyr Leu Ile
                165                 170                 175
Gly Gly Ile Ile Ser Gly Ile Leu Gly Met Leu Leu Leu Glu Ser Tyr
                180                 185                 190
Gly Trp Arg Pro Leu Met Leu Ile Gly Leu Pro Leu Ile Leu Leu
                195                 200                 205
Pro Ile Phe Met Arg Phe Leu Pro Glu Ser Pro Glu Trp Leu Ala Ser
                210                 215                 220
Lys Gly Arg Gln Ala Glu Ala Asp Gly Ile Cys Asp Ser Tyr Gly Leu
225                 230                 235                 240
Gln Arg Ile Val Pro His Ala Lys Met Gln Lys Gly Val Gly Ala
                245                 250                 255
Leu Phe Ser Glu Gly Arg Leu Ala Ser Thr Leu Asn Ala Trp Gly Ile
                260                 265                 270
His Phe Cys Ser Leu Leu Leu Thr Phe Gly Met Val Asn Trp Leu Pro
                275                 280                 285
Thr Ile Met Asn Lys Met Gly Tyr Asp Ile Ser Ser Ala Leu Ser Phe
                290                 295                 300
Ser Val Met Leu Asn Val Gly Ala Ala Ile Gly Ile Leu Ile Gly Gly
305                 310                 315                 320
Arg Phe Ala Asp Lys Gly Asn Val Lys Val Val Ala Ile Leu Phe
                325                 330                 335
Ala Val Gly Ala Ala Ser Ile Phe Ala Leu Thr Ala Asn Lys Gly Pro
                340                 345                 350
Leu Leu Tyr Val Phe Val Ala Leu Ala Gly Ala Gly Thr Ile Gly Thr
                355                 360                 365
Gln Ile Leu Ala Asn Val Leu Val Gly Arg Leu Tyr Pro Val His Ile
                370                 375                 380
Arg Gly Thr Gly Leu Gly Phe Ser Leu Ala Val Gly Arg Leu Gly Gly
385                 390                 395                 400
Ile Ala Gly Pro Met Ile Gly Gly Leu Val Leu Gln Arg Gly Leu Ala
                405                 410                 415
Pro Glu Trp Asn Phe Tyr Ile Phe Gly Ser Val Ala Val Gly Leu
                420                 425                 430
Met Leu Thr Val Leu Thr Leu Leu Tyr Arg Thr Ser Gly Asp Ala Arg
                435                 440                 445
```

Val

<210> SEQ ID NO 7
<211> LENGTH: 56
<212> TYPE: DNA
<213> ORGANISM: Artificial Sequence
<220> FEATURE:
<223> OTHER INFORMATION: PCR primer

<400> SEQUENCE: 7
gctgagctca catgtcagga ggtaataaat atgaataaac aaggaaatca aatgtc     56

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
ctaggatcct tatccaatca cttcagcccc ag     32

<210> SEQ ID NO 9
<211> LENGTH: 42
<212> TYPE: DNA
<213> ORGANISM: Artificial Sequence
<220> FEATURE:
<223> OTHER INFORMATION: PCR primer

<400> SEQUENCE: 9
gctggatcca ggaggtaata catatgggca ataccaatgg ag     42

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
gcagtcgact tacatgattt tgctttctgt tcc     33

<210> SEQ ID NO 11
<211> LENGTH: 59
<212> TYPE: DNA
<213> ORGANISM: Artificial Sequence
<220> FEATURE:
<223> OTHER INFORMATION: PCR primer

<400> SEQUENCE: 11
cgagaattcc atggcaggag gtaataaata tgtccacatc agatagttgt tataatacg     59

<210> SEQ ID NO 12
<211> LENGTH: 33
<212> TYPE: DNA
<213> ORGANISM: Artificial Sequence
<220> FEATURE:
<223> OTHER INFORMATION: PCR primer

<400> SEQUENCE: 12
gatggatcct taatcagaat aacgttcggt ttg     33

<210> SEQ ID NO 13
<211> LENGTH: 44
<212> TYPE: DNA

<213> ORGANISM: Artificial Sequence
<220> FEATURE:
<223> OTHER INFORMATION: PCR primer

<400> SEQUENCE: 13
gctggatcca ggaggtaata catatgtctc agagaagtaa gtac        44

<210> SEQ ID NO 14
<211> LENGTH: 35
<212> TYPE: DNA
<213> ORGANISM: Artificial Sequence
<220> FEATURE:
<223> OTHER INFORMATION: PCR primer

<400> SEQUENCE: 14
gcagtcgact taggctatta catcgcgacg tttcc        35

<210> SEQ ID NO 15
<211> LENGTH: 52
<212> TYPE: DNA
<213> ORGANISM: Artificial Sequence
<220> FEATURE:
<223> OTHER INFORMATION: PCR primer

<400> SEQUENCE: 15
cgtgaattcc atggcaggag gtaataaata tgaatatcat gcagccgtta ag        52

<210> SEQ ID NO 16
<211> LENGTH: 33
<212> TYPE: DNA
<213> ORGANISM: Artificial Sequence
<220> FEATURE:
<223> OTHER INFORMATION: PCR primer

<400> SEQUENCE: 16
gctggatcct aaggtgaga gctcttccag gac        33

<210> SEQ ID NO 17
<211> LENGTH: 43
<212> TYPE: DNA
<213> ORGANISM: Artificial Sequence
<220> FEATURE:
<223> OTHER INFORMATION: PCR primer

<400> SEQUENCE: 17
cgtggatcca ggaggtaata catatgcagg gacggggaga cgc        43

<210> SEQ ID NO 18
<211> LENGTH: 34
<212> TYPE: DNA
<213> ORGANISM: Artificial Sequence
<220> FEATURE:
<223> OTHER INFORMATION: PCR primer

<400> SEQUENCE: 18
gcagtcgact taaacccgtg cgtcgcccga tgtg        34

<210> SEQ ID NO 19
<211> LENGTH: 28
<212> TYPE: DNA
<213> ORGANISM: Artificial Sequence
<220> FEATURE:
<223> OTHER INFORMATION: PCR primer

<400> SEQUENCE: 19
cgatcatgaa agcacgtgtg tcttgttc        28

<210> SEQ ID NO 20
<211> LENGTH: 32
<212> TYPE: DNA
<213> ORGANISM: Artificial Sequence
<220> FEATURE:
<223> OTHER INFORMATION: PCR primer

<400> SEQUENCE: 20
gcagagctct tactgataca gtgccggacg ag                          32

<210> SEQ ID NO 21
<211> LENGTH: 360
<212> TYPE: PRT
<213> ORGANISM: Agrobacterium tumefaciens

<400> SEQUENCE: 21

```
Met Lys Ala Arg Val Ser Cys Ser Ala Lys Pro Gly Asp Met Ser Pro
1               5                   10                  15

Asn Thr Gly Asn Glu Val Phe Gln Met Thr Val Lys Ile Gly Val Ile
            20                  25                  30

Gly Thr Gly Ala Ile Gly Arg Asp His Ala Arg Arg Ile Asn Glu Val
        35                  40                  45

Leu Gly Gly Ala Lys Val Val Ala Leu Ser Asp Val Asn Arg Ala Ser
    50                  55                  60

Ser Glu Ala Val Lys Lys Asp Ile Ala Pro Asp Ala Ala Ile Phe Ala
65                  70                  75                  80

Thr Gly Glu Glu Leu Ile Ala Ser Ala Asp Val Asp Ala Val Leu Val
                85                  90                  95

Thr Ser Trp Gly Ala Thr His Glu Gln Tyr Val Leu Ala Ala Ile Ala
            100                 105                 110

Ala Gly Lys Pro Cys Phe Cys Glu Lys Pro Leu Ala Thr Thr Ala Glu
        115                 120                 125

Gly Ala Lys Arg Ile Val Asp Ala Glu Val Ala Leu Gly Lys Arg Leu
    130                 135                 140

Val Gln Val Gly Phe Met Arg Arg Tyr Asp Ala Gly Tyr Val Ala Leu
145                 150                 155                 160

Lys Lys Thr Val Asp Thr Met Ile Gly Ala Pro Ile Met Val His Ala
                165                 170                 175

Ala His Arg Asn Pro Thr Val Pro Glu Gln Tyr Val Thr Pro Met Ala
            180                 185                 190

Ile His Asp Thr Met Ile His Glu Ile Asp Val Leu Arg Trp Leu Leu
        195                 200                 205

Asp Asp Asp Tyr Val Ser Ala Arg Val Leu Phe Pro Arg Ala Ala Ala
    210                 215                 220

Arg Ser His Ala Lys Leu Arg Asp Pro Gln Ile Val Ile Leu Glu Thr
225                 230                 235                 240

Ala Arg Gly Thr Ile Ile Asp Val Glu Ile Phe Val Asn Cys His Tyr
                245                 250                 255

Gly Tyr Asp Ile Gln Cys Gln Val Val Gly Glu Asp Gly Ile Ala Ser
            260                 265                 270

Leu Pro Glu Pro Met Ala Ile Gln Thr Arg Leu Gly Ala Lys Leu Gln
        275                 280                 285

Asn Asp Ile Leu Thr Asp Trp Lys Asp Arg Phe Ile Ala Ser Tyr Asp
    290                 295                 300

Val Glu Leu Gln Asp Phe Ile His Ala Ala Ala Lys Gly Thr Ala Ser
```

```
305                 310                 315                 320

Gly Pro Asn Ser Trp Asp Gly Tyr Val Ala Ala Ile Thr Ser Asp Ala
                325                 330                 335

Cys Val Ala Ala Gln Glu Thr Asp Gly Ala Ala Val Ala Ile Arg Leu
                340                 345                 350

Pro Thr Arg Pro Ala Leu Tyr Gln
                355                 360

<210> SEQ ID NO 22
<211> LENGTH: 261
<212> TYPE: PRT
<213> ORGANISM: Agrobacterium tumefaciens

<400> SEQUENCE: 22

Met Arg Phe Ala Ile Asn His Ile Thr Ala Pro Ala Leu Ser Leu Glu
1               5                   10                  15

Asp Phe Phe Gln Thr Ala Arg Glu Leu Gly Leu Thr Glu Val Glu Ile
                20                  25                  30

Arg Asn Asp Leu Pro Asp Ile Val Gly Thr Val Thr Pro Ala Gln Val
            35                  40                  45

Lys Ala Ala Asp Lys Ala Gly Val Thr Ile Ser Ile Asn Ala
    50                  55                  60

Leu Tyr Pro Phe Asn Val Trp Ser Gly Asp Leu Pro Gln Arg Ala Val
65                  70                  75                  80

Ala Met Ala Asp Tyr Ala Ala Ala Ser Gly Ala Lys Ala Leu Val Met
                85                  90                  95

Cys Pro Leu Asn Asp Gly Arg Ala Val Ser Phe Asp Asp Leu Val Thr
                100                 105                 110

Ala Leu Lys Ala Met Lys Pro Ile Leu Glu Glu Arg Gly Leu Thr Gly
            115                 120                 125

Leu Val Glu Pro Leu Gly Phe Pro Val Ser Ser Leu Arg Thr Lys Thr
        130                 135                 140

Glu Ala Val Arg Ala Ile Asp Val Ala Gly Gly Asp Val Tyr Arg
145                 150                 155                 160

Leu Val His Asp Thr Phe His His His Leu Ala Gly Glu Thr Ala Phe
                165                 170                 175

Phe Pro Glu Arg Thr Gly Leu Val His Ile Ser Gly Val Thr Asp Pro
                180                 185                 190

Ala Val Ser Val Ala Asp Met Leu Asp Ala His Arg Val Leu Val Asp
            195                 200                 205

Gly Ala Asp Arg Leu Glu Asn Ile Ala Gln Ile Arg Ala Leu Glu Ala
        210                 215                 220

Ala Gly Tyr Lys Gly Pro Tyr Ser Phe Glu Pro Phe Ala Thr Glu Val
225                 230                 235                 240

His Asp Leu Lys Asp Pro Ala Ala Val Lys Ala Ser Ile Asp His
                245                 250                 255

Ile Ala Gly Ala Leu
        260

<210> SEQ ID NO 23
<211> LENGTH: 367
<212> TYPE: PRT
<213> ORGANISM: Agrobacterium tumefaciens

<400> SEQUENCE: 23

Met Pro Gly Lys Thr Ala Ser Met Lys Ala Arg Val Ser Cys Ser Ala
```

```
  1               5                  10                 15
Lys Pro Gly Asp Thr Ser Pro Asn Thr Gly Asn Glu Val Phe Gln Met
            20                  25                 30

Thr Val Arg Ile Gly Val Val Gly Thr Gly Ala Ile Gly Arg Asp His
            35                  40                 45

Ala Arg Arg Ile Asn Lys Val Leu Gly Gly Ala Lys Ile Val Ala Leu
 50                  55                  60

Ser Asp Val Asn Arg Ala Ser Ala Glu Ala Val Lys Asn Asp Ile Ala
 65                  70                  75                 80

Pro Asp Ala Val Leu Phe Ala Thr Gly Glu Glu Leu Ile Ala Ser Pro
            85                  90                 95

Asp Val Glu Ala Val Leu Val Thr Ser Trp Gly Ala Thr His Glu Gln
           100                 105                110

Tyr Val Leu Ala Ala Ile Ala Ala Gly Lys Pro Cys Phe Cys Glu Lys
           115                 120                125

Pro Leu Ala Thr Thr Ala Glu Gly Ala Arg Arg Ile Val Asp Ala Glu
           130                 135                140

Val Ala His Gly Lys Arg Leu Val Gln Val Gly Phe Met Arg Arg Tyr
145                 150                 155                160

Asp Ala Gly Tyr Val Ala Leu Lys Gln Ala Val Asp Asn Arg Ile Gly
            165                 170                175

Ala Pro Ile Met Val His Ala Ala His Arg Asn Pro Ser Val Pro Glu
            180                 185                190

Gln Tyr Val Thr Pro Met Ala Ile His Asp Thr Met Ile His Glu Ile
            195                 200                205

Asp Val Leu Arg Trp Leu Leu Asp Asp Tyr Val Ser Ala Arg Val
210                 215                 220

Leu Phe Pro Arg Ser Ala Ala Arg Ser His Ala Lys Leu Lys Asp Pro
225                 230                 235                240

Gln Ile Val Ile Leu Glu Thr Ala Lys Gly Thr Ile Ile Asp Val Glu
            245                 250                255

Ile Phe Val Asn Cys His Tyr Gly Tyr Asp Ile Gln Cys Gln Val Val
            260                 265                270

Gly Glu Asp Gly Ile Ala Ser Leu Pro Glu Pro Met Ser Val Gln Thr
            275                 280                285

Arg Leu Gly Ala Arg Leu Gln Asn Asp Ile Leu Thr Asp Trp Lys Asp
290                 295                 300

Arg Phe Ile Ala Ser Tyr Asp Val Glu Leu Gln Asp Phe Ile His Ala
305                 310                 315                320

Ala Ala Lys Gly Thr Ala Ser Gly Pro Asn Ser Trp Asp Gly Tyr Val
            325                 330                335

Ala Ala Ile Ser Ser Asp Ala Cys Val Ala Ala Gln Glu Thr Gln Gly
            340                 345                350

Ala Ala Val Ala Ile Asp Leu Pro Ala Arg Pro Ala Leu Tyr Gln
            355                 360                365

<210> SEQ ID NO 24
<211> LENGTH: 265
<212> TYPE: PRT
<213> ORGANISM: Agrobacterium tumefaciens

<400> SEQUENCE: 24

Met Arg Ser Phe Met Arg Phe Ala Ile Asn His Ile Thr Ala Pro Lys
1               5                  10                 15
```

Leu Ser Leu Glu Gln Phe Phe Ala Thr Ala Arg Glu Leu Gly Leu Ala
            20                  25                  30

Glu Val Glu Ile Arg Asn Asp Leu Pro Asp Ile Val Gly Thr Val Asp
        35                  40                  45

Pro Ala Ala Val Lys Ala Ala Glu Lys Ala Gly Val Thr Ile Ile
50                  55                  60

Ser Ile Asn Ala Leu Tyr Pro Phe Asn Val Trp Ser Gly Asp Leu Pro
65                  70                  75                  80

Ala Arg Ala Val Ala Met Ala Asp Tyr Ala Ala Ser Gly Ala Asn
                85                  90                  95

Ala Leu Val Met Cys Pro Leu Asn Asp Gly Thr Ala Val Ser Phe Asp
            100                 105                 110

Asn Leu Val Thr Ala Leu Lys Ala Met Lys Leu Ile Leu Glu Glu Arg
            115                 120                 125

Gly Leu Thr Gly Leu Val Glu Pro Leu Gly Phe Pro Val Ser Ser Leu
130                 135                 140

Arg Thr Lys Ala Glu Ala Val Arg Ala Ile Asp Ala Ala Gly Gly Gly
145                 150                 155                 160

Asp Val Tyr Lys Leu Val His Asp Thr Phe His His His Leu Ala Gly
                165                 170                 175

Glu Thr Glu Leu Phe Pro Glu Arg Thr Gly Leu Val His Ile Ser Gly
            180                 185                 190

Val Thr Asp Pro Ala Val Ser Val Ala Asp Met Leu Asp Ala His Arg
            195                 200                 205

Val Leu Val Asp Gly Asp Asp Arg Leu Glu Asn Ile Ala Gln Ile Lys
    210                 215                 220

Thr Leu Glu Ala Ala Gly Tyr Lys Gly Pro Tyr Ser Phe Glu Pro Phe
225                 230                 235                 240

Ala Thr Glu Val His Glu Leu Lys Asp Pro Ala Val Val Lys Asp
                245                 250                 255

Ser Ile Asp His Ile Ser Arg Ala Leu
            260                 265

<210> SEQ ID NO 25
<211> LENGTH: 344
<212> TYPE: PRT
<213> ORGANISM: Bacillus subtilis

<400> SEQUENCE: 25

Met Ser Leu Arg Ile Gly Val Ile Gly Thr Gly Ala Ile Gly Lys Glu
1               5                   10                  15

His Ile Asn Arg Ile Thr Asn Lys Leu Ser Gly Ala Glu Ile Val Ala
            20                  25                  30

Val Thr Asp Val Asn Gln Glu Ala Gln Lys Val Val Glu Gln Tyr
        35                  40                  45

Gln Leu Asn Ala Thr Val Tyr Pro Asn Asp Ser Leu Leu Ala Asp
    50                  55                  60

Glu Asn Val Asp Ala Val Leu Val Thr Ser Trp Gly Pro Ala His Glu
65                  70                  75                  80

Ser Ser Val Leu Lys Ala Ile Lys Ala Gln Lys Tyr Val Phe Cys Glu
                85                  90                  95

Lys Pro Leu Ala Thr Thr Ala Glu Gly Cys Met Arg Ile Val Glu Glu
            100                 105                 110

Glu Ile Lys Val Gly Lys Arg Leu Val Gln Val Gly Phe Met Arg Arg
            115                 120                 125

Tyr Asp Ser Gly Tyr Val Gln Leu Lys Glu Ala Leu Asp Asn His Val
            130                 135                 140

Ile Gly Glu Pro Leu Met Ile His Cys Ala His Arg Asn Pro Thr Val
145                 150                 155                 160

Gly Asp Asn Tyr Thr Thr Asp Met Ala Val Val Asp Thr Leu Val His
                165                 170                 175

Glu Ile Asp Val Leu His Trp Leu Val Asn Asp Asp Tyr Glu Ser Val
            180                 185                 190

Gln Val Ile Tyr Pro Lys Lys Ser Lys Asn Ala Leu Pro His Leu Lys
        195                 200                 205

Asp Pro Gln Ile Val Val Ile Glu Thr Lys Gly Gly Ile Val Ile Asn
210                 215                 220

Ala Glu Ile Tyr Val Asn Cys Lys Tyr Gly Tyr Asp Ile Gln Cys Glu
225                 230                 235                 240

Ile Val Gly Glu Asp Gly Ile Ile Lys Leu Pro Glu Pro Ser Ser Ile
                245                 250                 255

Ser Leu Arg Lys Glu Gly Arg Phe Ser Thr Asp Ile Leu Met Asp Trp
            260                 265                 270

Gln Arg Arg Phe Val Ala Ala Tyr Asp Val Glu Ile Gln Asp Phe Ile
        275                 280                 285

Asp Ser Ile Gln Lys Lys Gly Glu Val Ser Gly Pro Thr Ala Trp Asp
290                 295                 300

Gly Tyr Ile Ala Ala Val Thr Thr Asp Ala Cys Val Lys Ala Gln Glu
305                 310                 315                 320

Ser Gly Gln Lys Glu Lys Val Glu Leu Lys Lys Pro Glu Phe Tyr
            325                 330                 335

Gln Ser Phe Thr Thr Val Gln Asn
        340

<210> SEQ ID NO 26
<211> LENGTH: 278
<212> TYPE: PRT
<213> ORGANISM: Bacillus subtilis

<400> SEQUENCE: 26

Met Lys Leu Cys Phe Asn Glu Ala Thr Thr Leu Glu Asn Ser Asn Leu
1               5                   10                  15

Lys Leu Asp Leu Glu Leu Cys Glu Lys His Gly Tyr Asp Tyr Ile Glu
            20                  25                  30

Ile Arg Thr Met Asp Lys Leu Pro Glu Tyr Leu Lys Asp His Ser Leu
        35                  40                  45

Asp Asp Leu Ala Glu Tyr Phe Gln Thr His His Ile Lys Pro Leu Ala
50                  55                  60

Leu Asn Ala Leu Val Phe Phe Asn Asn Arg Asp Glu Lys Gly His Asn
65                  70                  75                  80

Glu Ile Ile Thr Glu Phe Lys Gly Met Met Gly Thr Cys Lys Thr Leu
                85                  90                  95

Gly Val Lys Tyr Val Val Ala Val Pro Leu Val Thr Glu Gln Lys Ile
            100                 105                 110

Val Lys Glu Glu Ile Lys Lys Ser Ser Val Asp Val Leu Thr Glu Leu
        115                 120                 125

Ser Asp Ile Ala Glu Pro Tyr Gly Val Lys Ile Ala Leu Glu Phe Val
130                 135                 140

Gly His Pro Gln Cys Thr Val Asn Thr Phe Glu Gln Ala Tyr Glu Ile

```
                145                 150                 155                 160
Val Asn Thr Val Asn Arg Asp Asn Val Gly Leu Val Leu Asp Ser Phe
                    165                 170                 175

His Phe His Ala Met Gly Ser Asn Ile Glu Ser Leu Lys Gln Ala Asp
            180                 185                 190

Gly Lys Lys Ile Phe Ile Tyr His Ile Asp Asp Thr Glu Asp Phe Pro
                195                 200                 205

Ile Gly Phe Leu Thr Asp Glu Asp Arg Val Trp Pro Gly Gln Gly Ala
            210                 215                 220

Ile Asp Leu Asp Ala His Leu Ser Ala Leu Lys Glu Ile Gly Phe Ser
225                 230                 235                 240

Asp Val Val Ser Val Glu Leu Phe Arg Pro Glu Tyr Tyr Lys Leu Thr
                    245                 250                 255

Ala Glu Glu Ala Ile Gln Thr Ala Lys Lys Thr Thr Val Asp Val Val
            260                 265                 270

Ser Lys Tyr Phe Ser Met
        275

<210> SEQ ID NO 27
<211> LENGTH: 337
<212> TYPE: PRT
<213> ORGANISM: Corynebacterium glutamicum

<400> SEQUENCE: 27

Met Ser Lys Ser Leu Arg Val Gly Val Val Gly Ala Gly Ala Met Gly
1               5                   10                  15

Ala Asp His Ile Asp Arg Ile Asn Asn Arg Thr Ser Gly Ala His Ile
                20                  25                  30

Ser Ala Ile Ile Glu Pro Asp Ala Ala Arg Ala Ala Ala Ala Ala Glu
            35                  40                  45

Asp Ala Pro Gly Ala Gln Ala Phe Thr Arg Ile Glu Asp Ala Ile Ala
        50                  55                  60

Ala Asp Ala Val Asp Ala Val Leu Ile Ala Val Pro Gly Gln Phe His
65                  70                  75                  80

Glu Pro Val Leu Val Pro Ala Leu Glu Ala Gly Leu Pro Ile Leu Cys
                85                  90                  95

Glu Lys Pro Leu Thr Pro Asp Ser Glu Ser Ser Leu Arg Ile Val Glu
            100                 105                 110

Leu Glu Gln Lys Leu Asp Lys Pro His Ile Gln Val Gly Phe Met Arg
        115                 120                 125

Arg Phe Asp Pro Glu Tyr Asn Asn Leu Arg Lys Leu Val Glu Ser Gly
    130                 135                 140

Glu Ala Gly Glu Leu Leu Met Leu Arg Gly Leu His Arg Asn Pro Ser
145                 150                 155                 160

Val Gly Glu Ser Tyr Thr Gln Ser Met Leu Ile Thr Asp Ser Val Val
                165                 170                 175

His Glu Phe Asp Val Ile Pro Trp Leu Ala Gly Ser Arg Val Val Ser
            180                 185                 190

Val Glu Val Lys Tyr Pro Lys Thr Ser Ser Leu Ala His Ser Gly Leu
        195                 200                 205

Lys Glu Pro Ile Leu Val Ile Met Glu Leu Glu Asn Gly Val Leu Val
    210                 215                 220

Asp Val Glu Met Asn Val Asn Ile Gln Phe Gly Tyr Gln Val Ala Thr
225                 230                 235                 240
```

```
Glu Ala Val Phe Glu Lys Gly Leu Ala Arg Ile Gly Gln Pro Ser Gly
            245                 250                 255

Met Gln Arg Trp Arg Asp Gly Glu Phe Leu Ile Asn Glu His Thr Asp
    260                 265                 270

Phe Thr Thr Arg Phe Ala Thr Ala Tyr Asp Arg Gln Ile Gln Ser Trp
        275                 280                 285

Val Asp Ala Val His Glu Gly Thr Leu Val Ala Gly Pro Asn Ala Trp
290                 295                 300

Asp Gly Tyr Leu Val Ala Leu Ser Cys Glu Ala Gly Val Lys Ala Leu
305                 310                 315                 320

Asp Gly Gly Val Ile Pro Val Asp Ala Ala Pro Arg Pro Asp Phe Tyr
                325                 330                 335

Ala

<210> SEQ ID NO 28
<211> LENGTH: 337
<212> TYPE: PRT
<213> ORGANISM: Corynebacterium glutamicum

<400> SEQUENCE: 28

Met Lys Leu Gly Leu Tyr Asn Ala Ile Phe His Asp Arg Thr Leu Pro
1               5                   10                  15

Glu Ala Leu Ala Ala Ile Lys Ala Gly Leu Thr Gly Ile Glu Leu
            20                  25                  30

Asn Thr Gly Gly Phe Leu Pro Ala Thr His Ile Pro Thr Ile Asp Asp
        35                  40                  45

Ile Leu Val Ser Asp Asp Ala Arg Asp Glu Phe Leu Gly Ile Phe Glu
50                  55                  60

Gly Thr Gly Val Asp Ile Tyr Gly Leu Asn Cys Asn Gly Asn Pro Leu
65                  70                  75                  80

His Pro Asn Lys Ala Ile Gly Asp Lys His Ala Glu Asp Ile Arg Arg
                85                  90                  95

Ser Ile Arg Leu Ala Glu Arg Leu Gly Gln Asn Arg Val Val Thr Met
            100                 105                 110

Ser Gly Leu Pro Gly Gly Glu Pro Gly Ala Lys Tyr Thr Asn Trp Val
        115                 120                 125

Val Asn Ala Trp Asn Ser Ala Ala Leu Asp Val Leu Asp Tyr Gln Trp
130                 135                 140

Asp Ile Ala Ala Glu Phe Trp Arg Glu Thr Asp Arg Phe Ala Ala Asp
145                 150                 155                 160

His Gly Val Lys Val Ala Leu Glu Leu His Pro Gln Asn Ile Val Phe
                165                 170                 175

Asn Ser Ala Asp Val His Lys Leu Ile Asp Leu Thr Gly Ala Thr His
            180                 185                 190

Val Gly Val Glu Leu Asp Ala Ser His Leu Phe Trp Gln Gln Met Asp
        195                 200                 205

Pro Ile Ala Val Ile Asp His Leu Gly Glu Leu Ile Phe His Ala Ala
210                 215                 220

Ala Lys Asp Val Arg Val Asn Lys Glu Trp Ala Gln Leu Asn Gly Val
225                 230                 235                 240

Leu Asp Asn Ser Phe Arg Arg Leu Asp Pro Ser Glu Asn Arg Thr Asn
                245                 250                 255

Leu Gly Gly Asp Glu Trp Ala Asn Glu Trp Pro Lys Asn Ser Ala Trp
            260                 265                 270
```

```
Asp Phe Val Ala Leu Gly Arg Gly His Asp Val Ala Tyr Trp Thr Glu
            275                 280                 285

Phe Leu Arg Ala Leu His Arg Val Asp Pro Asn Met Leu Val Asn Ile
        290                 295                 300

Glu His Glu Asp Val Ser Leu Gly Arg Glu Glu Gly Val Asn Glu Ala
305                 310                 315                 320

Ala Lys Val Leu Ile Glu Ala Asn Lys Ala Leu Glu Glu Ser Leu Val
                325                 330                 335

Ser

<210> SEQ ID NO 29
<211> LENGTH: 336
<212> TYPE: PRT
<213> ORGANISM: Corynebacterium glutamicum

<400> SEQUENCE: 29

Met Ser Leu Lys Leu Gly Val Ile Gly Thr Gly Ala Ile Gly Gln Glu
1               5                   10                  15

His Ile Arg Arg Cys Asn Asn Val Leu Gln Gly Ala Arg Val Val Ala
            20                  25                  30

Val Ser Asp Ile Asn Val Glu Gly Ala Gln Ala Ala Leu Gln Arg Leu
        35                  40                  45

Asn Ser Asp Ala Gln Val Cys Lys Asp Gly Tyr Glu Val Ile Gln Ser
    50                  55                  60

Pro Asp Val Asp Ala Val Leu Val Thr Ser Trp Asp Pro Thr His Glu
65                  70                  75                  80

Glu Phe Thr Leu Ala Ala Ile Ala Ala Gly Lys Pro Val Phe Cys Glu
                85                  90                  95

Lys Pro Leu Ala Met Ser Ala Glu Gly Cys Arg Arg Val Glu Ala
            100                 105                 110

Glu Ile Gln His Gly Lys Arg Leu Val Gln Val Gly Phe Met Arg Pro
        115                 120                 125

Tyr Asp Ala Gly Tyr Arg Ala Leu Lys Lys Val Ile Thr Asp Gly Glu
    130                 135                 140

Ile Gly Glu Pro Leu Met Leu His Cys Ala His Arg Asn Pro Thr Val
145                 150                 155                 160

Pro Glu Asn Tyr Asn Thr Glu Met Ala Ile Thr Asn Thr Leu Ile His
                165                 170                 175

Glu Leu Asp Val Leu Arg Trp Leu Thr Ser Asp Asp Tyr Lys Ser Val
            180                 185                 190

Gln Val Val Phe Pro Arg Val Ser Ser Lys Ala Arg Pro His Leu Lys
        195                 200                 205

Asp Pro Gln Ile Val Leu Phe Glu Thr Gln Lys Gly Val Arg Ile Asp
    210                 215                 220

Val Glu Ile Phe Val Asn Cys Thr Tyr Gly Tyr Asp Ile Gln Cys Glu
225                 230                 235                 240

Val Val Gly Glu Glu Gly Ile Ala Arg Leu Pro Glu Pro Ser Ser Val
                245                 250                 255

Gln Leu Arg Lys Gln Ala Lys Leu Ser Asn Thr Ile Leu Val Asp Trp
            260                 265                 270

Lys Asp Arg Phe Ile Glu Ala Tyr Asp Val Glu Leu Gln Ala Phe Ile
        275                 280                 285

Asn Asp Val Lys Ala Gly Gln Leu Thr Gly Pro Ser Ala Trp Asp Gly
    290                 295                 300
```

```
Phe Ala Ala Ser Val Ala Asp Ala Cys Ile Lys Ala Gln Lys Ser
305                 310                 315                 320

Gly Ala Ile Glu Pro Ile Glu Met Pro Ala Arg Pro Ala Phe Tyr Asn
            325                 330                 335
```

<210> SEQ ID NO 30
<211> LENGTH: 273
<212> TYPE: PRT
<213> ORGANISM: Corynebacterium glutamicum

<400> SEQUENCE: 30

```
Met Thr Ile Ala Ala Glu Arg Phe Cys Ile Asn Arg Lys Ile Ala Pro
1               5                   10                  15

Ser Leu Ser Ile Glu Ala Phe Phe Arg Leu Val Asn Gly Leu Gly Leu
            20                  25                  30

Asn Lys Val Glu Leu Arg Asn Asp Leu Pro Ser Gly Asn Val Met Asp
        35                  40                  45

Asn Leu Ser Ala Ala Gln Val Cys Ala Leu Ala Glu Arg Tyr Gly Ile
50                  55                  60

Asp Ile Ile Thr Ile Asn Ala Val Tyr Pro Phe Asn Gln Arg Thr Glu
65                  70                  75                  80

Gln Val Arg Gln Leu Thr Glu Ser Leu Leu Ala Asp Ala Lys Ala Val
                85                  90                  95

Gly Ala Arg Ser Leu Val Leu Cys Pro Leu Asn Asp Gly Ser Ser Val
            100                 105                 110

Ala Pro Glu Val Thr Leu Asn Ala Leu Arg Asp Leu Ala Pro Leu Phe
        115                 120                 125

Ala Thr Tyr Gly Ile Thr Gly Leu Val Glu Pro Leu Gly Phe Pro Gln
130                 135                 140

Ser Ser Leu Arg Ser Ala Ala Gln Ala Gln Lys Leu Ile Arg Asp Ala
145                 150                 155                 160

His Val Pro Phe Lys Leu Leu Ile Asp Thr Phe His His His Leu Tyr
                165                 170                 175

Pro Asp Ala Asp Ala Glu Phe Ser Gln Val Asp Ile Ala Gln Ile Gly
            180                 185                 190

Leu Val His Leu Ser Gly Val Glu Asp Lys Arg Pro Arg Glu Ser Leu
        195                 200                 205

Thr Asp Ala Glu Arg Ile Met Leu Thr Pro Glu Asp Arg Leu Phe Thr
210                 215                 220

Cys Arg Gln Val Lys Gln Leu Glu Glu Arg Gly Tyr Lys Gly Ile Tyr
225                 230                 235                 240

Ala Phe Glu Pro Phe Ala Pro Glu Leu Ala Asp Trp Asp Glu Asn Lys
                245                 250                 255

Ile Gln His Glu Ile Lys Asn Ser Ile Gln Leu Ile Gln His Ser Leu
            260                 265                 270

Lys
```

<210> SEQ ID NO 31
<211> LENGTH: 335
<212> TYPE: PRT
<213> ORGANISM: Corynebacterium glutamicum

<400> SEQUENCE: 31

```
Met Thr Leu Arg Ile Ala Leu Phe Gly Ala Gly Arg Ile Gly His Val
1               5                   10                  15

His Ala Ala Asn Ile Ala Ala Asn Pro Asp Leu Glu Leu Val Val Ile
```

```
            20                  25                  30
Ala Asp Pro Phe Ile Glu Gly Ala Gln Arg Leu Ala Glu Ala Asn Gly
            35                  40                  45

Ala Glu Ala Val Ala Ser Pro Asp Glu Val Phe Ala Arg Asp Asp Ile
        50                  55                  60

Asp Gly Ile Val Ile Gly Ser Pro Thr Ser Thr His Val Asp Leu Ile
65                  70                  75                  80

Thr Arg Ala Val Glu Arg Gly Ile Pro Ala Leu Cys Glu Lys Pro Ile
                85                  90                  95

Asp Leu Asp Ile Glu Met Val Arg Ala Cys Lys Glu Lys Ile Gly Asp
            100                 105                 110

Gly Ala Ser Lys Val Met Leu Gly Phe Asn Arg Arg Phe Asp Pro Ser
        115                 120                 125

Phe Ala Ala Ile Asn Ala Arg Val Ala Asn Gln Glu Ile Gly Asn Leu
        130                 135                 140

Glu Gln Leu Val Ile Ile Ser Arg Asp Pro Ala Pro Ala Pro Lys Asp
145                 150                 155                 160

Tyr Ile Ala Gly Ser Gly Gly Ile Phe Arg Asp Met Thr Ile His Asp
                165                 170                 175

Leu Asp Met Ala Arg Phe Phe Val Pro Asn Ile Val Glu Val Thr Ala
            180                 185                 190

Thr Gly Ala Asn Val Phe Ser Gln Glu Ile Ala Glu Phe Asn Asp Tyr
        195                 200                 205

Asp Gln Val Ile Val Thr Leu Arg Gly Ser Lys Gly Glu Leu Ile Asn
        210                 215                 220

Ile Val Asn Ser Arg His Cys Ser Tyr Gly Tyr Asp Gln Arg Leu Glu
225                 230                 235                 240

Ala Phe Gly Ser Lys Gly Met Leu Ala Ala Asp Asn Ile Arg Pro Thr
                245                 250                 255

Thr Val Arg Lys His Asn Ala Glu Ser Thr Glu Gln Ala Asp Pro Ile
            260                 265                 270

Phe Asn Phe Phe Leu Glu Arg Tyr Asp Ala Ala Tyr Lys Ala Glu Leu
        275                 280                 285

Ala Thr Phe Ala Gln Gly Ile Arg Asp Gly Gln Gly Phe Ser Pro Asn
        290                 295                 300

Phe Glu Asp Gly Val Ile Ala Leu Glu Leu Ala Asn Ala Cys Leu Glu
305                 310                 315                 320

Ser Ala Gln Thr Gly Arg Thr Val Thr Leu Asn Pro Ala Asn Val
                325                 330                 335

<210> SEQ ID NO 32
<211> LENGTH: 31
<212> TYPE: DNA
<213> ORGANISM: Artificial Sequence
<220> FEATURE:
<223> OTHER INFORMATION: PCR primer

<400> SEQUENCE: 32
cgaacatgtc tatgcctggg aagaccgcgt c                          31

<210> SEQ ID NO 33
<211> LENGTH: 31
<212> TYPE: DNA
<213> ORGANISM: Artificial Sequence
<220> FEATURE:
<223> OTHER INFORMATION: PCR primer
```

<400> SEQUENCE: 33
gcagagctct tattggtaaa gtgcgggacg g        31

<210> SEQ ID NO 34
<211> LENGTH: 44
<212> TYPE: DNA
<213> ORGANISM: Artificial Sequence
<220> FEATURE:
<223> OTHER INFORMATION: PCR primer

<400> SEQUENCE: 34
ctaggatcca ggagatatac atatgaggtc tttcatgcgt tttg        44

<210> SEQ ID NO 35
<211> LENGTH: 33
<212> TYPE: DNA
<213> ORGANISM: Artificial Sequence
<220> FEATURE:
<223> OTHER INFORMATION: PCR primer

<400> SEQUENCE: 35
cgagtcgact tagagcgccc gggagatatg gtc        33

<210> SEQ ID NO 36
<211> LENGTH: 28
<212> TYPE: DNA
<213> ORGANISM: Artificial Sequence
<220> FEATURE:
<223> OTHER INFORMATION: PCR primer

<400> SEQUENCE: 36
gacacatgtc aatgagttta cgtattgg        28

<210> SEQ ID NO 37
<211> LENGTH: 32
<212> TYPE: DNA
<213> ORGANISM: Artificial Sequence
<220> FEATURE:
<223> OTHER INFORMATION: PCR primer

<400> SEQUENCE: 37
ctagcggccg ccttcatatt ttcactcctc tg        32

<210> SEQ ID NO 38
<211> LENGTH: 30
<212> TYPE: DNA
<213> ORGANISM: Artificial Sequence
<220> FEATURE:
<223> OTHER INFORMATION: PCR primer

<400> SEQUENCE: 38
cgacatatga aactttgttt taatgaagcg        30

<210> SEQ ID NO 39
<211> LENGTH: 38
<212> TYPE: DNA
<213> ORGANISM: Artificial Sequence
<220> FEATURE:
<223> OTHER INFORMATION: PCR primer

<400> SEQUENCE: 39
cgattaatta attacatgct gaagtatttt gatacgac        38

<210> SEQ ID NO 40
<211> LENGTH: 28

<210> SEQ ID NO 40
<211> LENGTH: (not shown)
<212> TYPE: DNA
<213> ORGANISM: Artificial Sequence
<220> FEATURE:
<223> OTHER INFORMATION: PCR primer

<400> SEQUENCE: 40
gactcatgag caagagcctt cgcgttgg                                    28

<210> SEQ ID NO 41
<211> LENGTH: 33
<212> TYPE: DNA
<213> ORGANISM: Artificial Sequence
<220> FEATURE:
<223> OTHER INFORMATION: PCR primer

<400> SEQUENCE: 41
ctagcggccg cctccttaag cgtagaaatc tgg                              33

<210> SEQ ID NO 42
<211> LENGTH: 28
<212> TYPE: DNA
<213> ORGANISM: Artificial Sequence
<220> FEATURE:
<223> OTHER INFORMATION: PCR primer

<400> SEQUENCE: 42
gttcatatga aactcggtct ctacaacg                                    28

<210> SEQ ID NO 43
<211> LENGTH: 33
<212> TYPE: DNA
<213> ORGANISM: Artificial Sequence
<220> FEATURE:
<223> OTHER INFORMATION: PCR primer

<400> SEQUENCE: 43
cgattaatta agtagttttt ttaagaaacc agg                              33

<210> SEQ ID NO 44
<211> LENGTH: 31
<212> TYPE: DNA
<213> ORGANISM: Artificial Sequence
<220> FEATURE:
<223> OTHER INFORMATION: PCR primer

<400> SEQUENCE: 44
gacacatgtc attgaaactt ggtgtgattg g                                31

<210> SEQ ID NO 45
<211> LENGTH: 32
<212> TYPE: DNA
<213> ORGANISM: Artificial Sequence
<220> FEATURE:
<223> OTHER INFORMATION: PCR primer

<400> SEQUENCE: 45
ctagcggccg cttagttata gaatgccgga cg                               32

<210> SEQ ID NO 46
<211> LENGTH: 26
<212> TYPE: DNA
<213> ORGANISM: Artificial Sequence
<220> FEATURE:
<223> OTHER INFORMATION: PCR primer

<400> SEQUENCE: 46
cgacatatga ccatcgccgc agaacg    26

<210> SEQ ID NO 47
<211> LENGTH: 31
<212> TYPE: DNA
<213> ORGANISM: Artificial Sequence
<220> FEATURE:
<223> OTHER INFORMATION: PCR primer

<400> SEQUENCE: 47
cgattaatta atgcatcaac gaagcctggg c    31

<210> SEQ ID NO 48
<211> LENGTH: 24
<212> TYPE: DNA
<213> ORGANISM: Artificial Sequence
<220> FEATURE:
<223> OTHER INFORMATION: PCR primer

<400> SEQUENCE: 48
gactcatgac tcttcgtatc gccc    24

<210> SEQ ID NO 49
<211> LENGTH: 33
<212> TYPE: DNA
<213> ORGANISM: Artificial Sequence
<220> FEATURE:
<223> OTHER INFORMATION: PCR primer

<400> SEQUENCE: 49
ctagcggccg cttaactaga cgttgactaa acg    33

<210> SEQ ID NO 50
<211> LENGTH: 1080
<212> TYPE: DNA
<213> ORGANISM: Agrobacterium tumefaciens

<400> SEQUENCE: 50
atgaaagcac gtgtgtcttg ttctgcaaaa cctggtgata tgtcccctaa tactggcaac    60
gaagtattcc agatgaccgt aaaaattggt gtgatcggta ctggtgctat ggccgcgac    120
cacgctcgcc gcatcaacga ggttctgggt ggcgctaaag tggtcgcact gtctgacgtg    180
aatcgcgcgt ccagcgaggc ggtaaaaaag gacattgcgc ctgacgccgc catcttcgcg    240
accggcgaag aactgatcgc cagcgctgac gtcgatgcgg tgctggtcac ttcctggggc    300
gctactcacg agcaatacgt actggcagct atcgcggcag gtaagccgtg cttctgcgaa    360
aaaccgctgg caaccactgc tgaaggtgct aagcgcattg ttgatgcgga ggttgcactg    420
ggtaaacgcc tggtccaagt aggtttcatg cgccgctacg acgccggtta tgttgcgctg    480
aaaaagaccg ttgataccat gattggcgct ccgatcatgg ttcatgctgc gcaccgcaac    540
ccgaccgtac cggaacagta cgtgaccccg atggcaatcc acgacactat gattcacgag    600
atcgacgtac tgcgttggct gctggatgat gattacgtgt ctgcgcgtgt cctgttcccg    660
cgtgcagcgg ctcgcagcca cgctaaactg cgcgatccgc aaattgttat cctggaaact    720
gcacgtggta ctatcatcga tgtagaaatc ttcgtgaact gccactacgg ctacgacatc    780
cagtgccagg ttgttggcga ggatggcatc gcctccctgc cggaaccgat ggcgatccag    840
acccgtctgg gtgctaagct gcaaaacgac attctgaccg actggaaaga ccgcttcatc    900
gcgtcttatg atgttgaact gcaagacttc attcacgcag cagcaaaagg caccgccagc    960
ggtccgaact cttgggacgg ctacgttgcg gcgatcacct ccgacgcttg cgttgctgct    1020

-continued

```
caagaaaccg acggtgcggc tgttgcgatc cgtctgccga ctcgtccggc actgtatcag    1080

<210> SEQ ID NO 51
<211> LENGTH: 811
<212> TYPE: DNA
<213> ORGANISM: Agrobacterium tumefaciens

<400> SEQUENCE: 51
ggatccagga gatatacata tgcgttttgc tattaaccat attactgctc cggcactgtc      60
tctggaagac ttttccaga ctgcgcgtga actgggcctg accgaagtgg aaatccgcaa     120
cgacctgccg gacatcgtcg gtactgtgac tcctgctcag gttaaagctg ctgctgataa     180
agccggtgta accattatct ccatcaacgc tctgtacccg ttcaacgtct ggagcggcga     240
cctgccgcag cgtgcagttg caatggctga ctatgcggct gcgtctggcg ccaaagctct     300
ggtcatgtgt ccgctgaacg atggtcgcgc ggtatctttt gatgacctgg taaccgctct     360
gaaagcgatg aagccgatcc tggaggaacg tggtctgact ggtctggtag agccgctggg     420
tttcccggtg tcttctctgc gtactaaaac cgaagcggtg cgtgcaatcg atgttgcagg     480
cggcggtgac gtgtatcgcc tggtccacga caccttccac caccacctgg cgggtgaaac     540
tgccttcttc ccggaacgca ccggtctggt tcacatcagc ggtgtcaccg acccagcagt     600
gtctgttgcg gacatgctgg acgcgcaccg tgtgctggtg gacggcgcag atcgcctgga     660
aaatatcgca cagattcgtg cgctggaagc agcgggttac aaaggtccgt attccttcga     720
accattcgct accgaagtgc acgacctgaa ggacccagcg gcggcggtta aagcgtctat     780
cgaccacatc gcaggtgcac tgtaagtcga c                                    811
```